US006214333B1

(12) United States Patent
Zoldhelyi et al.

(10) Patent No.: US 6,214,333 B1
(45) Date of Patent: Apr. 10, 2001

(54) VASOPROTECTIVE RECOMBINANT ADENOVIRUS VECTOR CONTAINING A HUMAN TFPI GENE

(75) Inventors: Pierre Zoldhelyi, Bellaire; James T. Willerson, Houston, both of TX (US)

(73) Assignee: Texas Heart Institute, Houston, TX (US)

( * ) Notice: Subject to any disclaimer, the term of this patent is extended or adjusted under 35 U.S.C. 154(b) by 0 days.

(21) Appl. No.: 09/013,366

(22) Filed: Jan. 26, 1998

Related U.S. Application Data

(60) Provisional application No. 60/051,887, filed on Jul. 8, 1997.

(51) Int. Cl.$^7$ .............................. A61K 48/00; C12N 5/10; C12N 15/861; C12N 15/64
(52) U.S. Cl. ...................... 424/93,1; 424/93.2; 424/93.6; 424/93.21; 435/320.1; 435/325; 435/69.6; 435/455; 435/456; 435/366; 435/372; 435/372.1; 435/91.4; 435/91.41
(58) Field of Search .................... 424/93.1, 93.2, 424/93.6, 93.21; 435/320.1, 69.1, 69.6, 455, 456, 325, 366, 372, 372.1, 91.4, 91.41

(56) References Cited

U.S. PATENT DOCUMENTS

| | | | |
|---|---|---|---|
| 4,966,852 | 10/1990 | Wun et al. | 435/320.1 |
| 5,106,833 | 4/1992 | Broze, Jr. et al. | 514/12 |
| 5,212,091 | 5/1993 | Diaz-Collier et al. | 435/69.6 |
| 5,427,926 | 6/1995 | Buonassisi et al. | 435/69.6 |
| 5,563,123 | 10/1996 | Innis et al. | 514/12 |

FOREIGN PATENT DOCUMENTS 9124506   5/1997   (JP) .

OTHER PUBLICATIONS

Girard et al., Tissue Factor Pathway Inhibitor, *Methods in Enzymology*. 1993, vol. 222, pp. 195–208.

Gnudi et al., Adenovirus–Mediated Gene Transfer of Dominant Negative Ras(asn17) in 3T3L1 Adipocytes does not Alter Insulinstimulated p. 13–Kinase Activity or Glucose Transport. *Molecular Endocrinology*. Jan. 1997, vol. 11, No. 1, pp. 67–76.

Gomez–Foix et al., Adenovirus–Mediated Transfer of the Muscle Glycogen Phosphorylase Gene into Hepatocytes Confers Altered Regulation of Glycogen Metabolism. *Journal of Biological Chemistry*. Dec. 15, 1992, vol. 267, No. 35, pp. 25129–25134.

Jude et al., Factuer Tissulaire et Maladie Coronaire (Tissue Factor and Coronary Disease). *Sang Thrombose Vaisseaux* (Aug. 10, 1996), pp. 629–634. [English language abstract only].

Lee, et al., In Vivo Adenoviral Vector–Mediated Gene Transfer into Balloon–Injured Rat Carotid Arteries, *Circulation Research*, vol. 73, No. 5, Nov. 1993, pp. 797–807.

Wun et al., Cloning and Characterization of a cDNA Coding for the Lipoprotein–Associated Coagulation Inhibitor Shows that it Consists of Three Tandem Kunitz–Type Inhibitory Domains. *Journal of Biological Chemistry*. May 5, 1988, vol. 263, No. 13, pp. 6001–6004.

Zoldhelyi, et al., Prevention of Arterial Thrombosis by Adenovirus–Mediated Transfer of Cyclooxygenase Gene, *Circulation*, vol. 93, No. 1, Jan. 1, 1996, pp. 10–17.

*Primary Examiner*—David Guzo
(74) *Attorney, Agent, or Firm*—McDaniel & Associates, P.C.; C. Steven McDaniel; Elizabeth R. Hall

(57) ABSTRACT

A recombinant adenoviral vector encoding the human tissue factor pathway inhibitor (TFPI) gene is disclosed which is useful for transduction of vascular smooth muscle cells at a selected blood vessel site to provide local vascular expression of TFPI. A method of using the transduced hTFPI cDNA as an in vivo antithrombotic agent to provide localized production of hTFPI for protecting an at-risk site against thrombus deposition is also disclosed. Gene therapy using the new TFPI expression vector is also expected to deter the development of chronic vascular stenosis in blood vessels (arteries, veins, arteriovenous shunts, and endovascular grafts) and deterring intimal hyperplasia.

28 Claims, 7 Drawing Sheets

(3 of 7 Drawing Sheet(s) Filed in Color)

VASOPROTECTIVE RECOMBINANT ADENOVIRUS VECTOR CONTAINING A HUMAN TFPI GENE

CROSS-REFERENCE TO RELATED APPLICATIONS

This application claims the benefit of U.S. Provisional Patent Application Ser. No. 60/051,887 filed Jul. 8, 1997, entitled "Vasoprotective Transgenic Tissue Factor Pathway Inhibitor."

STATEMENT REGARDING FEDERALLY SPONSORED RESEARCH OR DEVELOPMENT

Not Applicable

BACKGROUND OF THE INVENTION

1. Field of the Invention

The present invention generally relates to agents that effect vasoprotection in mammals. More particularly, the invention pertains to anti-thrombotic agents that are adapted for localized rather than systemic administration. Still more particularly, the invention relates to recombinant adenovirus vectors containing a DNA sequence encoding a human tissue factor pathway inhibitor (TFPI) gene and to methods of making and using such vectors to effect local expression of TFPI in vascular smooth muscle cells at a specific blood vessel site.

2. Description of the Related Art

Pharmacological anticoagulation therapies are widely employed to deter thrombus formation in injured or atherosclerotic arteries. These therapeutic approaches typically employ physiological inhibitors of thrombin and require systemic administration of multiple drugs. However, the presence of anticoagulants in the circulating (systemic) blood is generally associated with increased bleeding risk. For instance, in clinical trials studying heparin and the thrombin inhibitor desirudin, most patients with acute coronary syndromes who developed intracranial bleeds had received aspirin, heparin or desirudin, and a thrombolytic agent (1–3). Those trials indicated that systemic blockade of multiple platelet/coagulation pathways is not without risk. Similarly, it is known that high doses of heparin are poorly tolerated in conjunction with potent platelet inhibition with c7E3 Fab (ReoPro) (4).

Short Term Local Administration of Antithrombotics

Since most conventional methods aimed at deterring thrombosis deposition act systemically and typically cause bleeding, some recent research efforts have focused on determining the feasibility of local anticoagulant treatment of predetermined "at risk" arterial sites, as opposed to treating the entire circulatory system. Local delivery of anticoagulant drugs has been attempted.

For example, the isolation of a portion of a vessel with a pair of angioplasty balloons and instillation of hirudin or heparin has been reported (4a). However, these methods are limited by uncertain drug delivery (given the systemic escape) and the short persistence of the antithrombotic drug in the vessel wall, given the diffusion gradient towards the vessel lumen. However, even in these localized treatments, no locally delivered antithrombotic drug has been reported to be present at the target site 48 hours after delivery. Points within the human circulatory system that are subject to injury, inflammation or atherosclerosis are especially likely targets for the local application of therapeutic anticoagulant agents, and include such specific sites as those subjected to angioplasty, stent or graft placement, or arteriovenous shunt.

For the purposes of this disclosure, "local" treatment, as distinguished from "systemic" treatment, means that a specific region, site or area within the blood circulatory system (especially a blood vessel) is the focus or target of the treatment and therefore receives the significant part of the treating agent, while the rest of the vessel and/or the circulatory system receive none or only an insignificant exposure to the treating agent. Short-term administration of antithrombins does little to passivate the injured artery, and allows thrombin generation to relentlessly proceed. In prior studies, for instance, it was found that short-term administration of the direct antithrombins failed to reduce restenosis rates after percutaneous coronary balloon angioplasty (5,6). This may be explained in part by experimental and clinical evidence suggesting that the thrombin inhibitors are not capable of inhibiting thrombin generation in the course of arterial thrombosis or in systemic procoagulant states (7,8). Furthermore, after withdrawal of short-term thrombin inhibitor therapy at 3–5 days, thrombin activity soon recurs (9,10).

Similar conclusions can be drawn from trials of short-term administration of synthetic inhibitors of GP IIb/IIIa integrin receptor (11). The administration of platelet IIb/IIIa integrin receptor blocker, c7E3 Fab (ReoPro), was effective in reducing early ischemic events in an early trial (12) and reduced the need for recurrent revascularization at 6-months. However, this was associated with increased bleeding at the time of the initial intervention (4). In a later trial, however, ReoPro failed to reduce the need for repeated revascularization at 6 months (13).

In summary, while effective during their administration, systemically given antithrombotic drugs are associated with increased hemorrhagic risk and require hospitalization associated with high cost, inconvenience, and additional risk of (hospital-acquired) infection; and, finally, do not passivate the thrombogenic lesion after the drug infusion is stopped (typically 3–5 days).

Anti-thrombotic Gene Therapy

Recent trials of systemic antithrombins to prevent restenosis after percutaneous revascularization suggest that there may be advantages to local antithrombotic gene therapy, which conventional drug therapy cannot presently match (5,6). Gene therapy potentially ensures the continuous in situ production of the foreign antithrombotic protein. Lee et al., in 1993, demonstrated that a replication-defective recombinant adenovirus can serve as an efficient vector for direct in vivo arterial gene transfer (14). Zoldhelyi et al. have previously described the adenovirus-mediated transfer of the cyclooxygenase gene (Ad.COX-1) as a localized antithrombotic agent (15). Cyclooxygenase is the rate-limiting enzyme in the synthesis of prostacyclin, an important vasoprotective molecule that inhibits platelet aggregation and vasoconstriction. Delivery of recombinant adenovirus to the artery at the doses used in the Ad.COX-1 study was associated with only minimal inflammation (15). Ad.COX-1 is a reasonable antithrombotic agent but has no direct influence on the thrombin-coagulation pathway involved in fibrin formation and smooth muscle cell proliferation contributing to restenosis after percutaneous balloon angioplasty. Also, platelet aggregation plays little role in venous thrombosis where thrombin inhibition is a highly effective approach (16).

Tissue Factor Pathway Inhibitor

Another approach to blockading platelet/coagulation pathways involves inhibiting thrombin activation via the tissue factor metabolic pathway. Tissue factor (TF), the cellular initiator of blood coagulation, is a transmembrane protein receptor exposed after vessel injury or after cytokine activation of endothelial cells and monocytes. Blood coagulation in the extrinsic pathway begins when the serine protease, activated factor VII (factor VIIa), which binds to its cofactor, TF, and the factor VIIa/TF enzyme complex activates by limited proteolysis of coagulation factors X and IX (17–19). On the membranes of activated platelets and endothelium, factor Xa then binds to factor Va, forming the prothrombinase complex, which in the presence of $Ca^{2+}$ proteolytically converts prothrombin to thrombin (20). Factor IXa, also activated by the factor VIIa/TF complex, combines with factor VIIIa to activate in a second (intrinsic) pathway factor X. Thus, TF plays an initiating role for both the extrinsic and intrinsic pathway of thrombin generation (21).

Thrombin, the final product of the converging coagulation pathways, activates platelets and converts fibrinogen to fibrin, thereby stimulating formation of the fibrin-platelet clot. Thrombin not only activates platelets, converts fibrinogen to fibrin, and via factor XIII activation, stabilizes the fibrin clot, but also positively feeds back on its generation by activating platelets, factors V, VIII and XI (22–24). In addition, thrombin promotes release of P-selectin from storage granules of platelets and endothelial cells, contributing to platelet-leukocyte interaction and leukocyte rolling and migration into the vessel wall (25). Thrombin-activation of platelets promotes exposure of the platelet IIb/IIIb integrin receptor (26). Activation of this receptor mediates platelet-platelet and platelet-vessel wall interactions and, by recruiting additional platelets, thrombin allows for its generation to be further amplified.

Tissue factor pathway inhibitor (TFPI) inhibits thrombin generation at several steps. TFPI inhibits factor VIIa/TF, thereby initiating thrombin generation after vascular injury or cell activation by cytokines, and also inhibits the factor Xa/prothrombinase complex, thereby interrupting thrombin generation at its major amplification step (27,28).

The mature TFPI is composed of 276 amino acids and contains three tandem Kunitz-type protease inhibitory domains, in addition to an acidic amino-terminal and a basic carboxy-terminal region (27–29). End-linked glycosylation occurs at one or more of three potential sites, but the role of this and other post-translational modifications is not yet known (27,30).

Initially, the second Kunitz-type domain interacts with factor Xa, by binding with 1:1 stoichiometry at or near the factor Xa active serine site. This TFPI/factor Xa interaction, then, promotes efficient binding of the first Kunitz-type domain to the factor VIIa/TF complex, resulting in a quaternary factor Xa/TFPI/factor VIIa/TF complex (27,28,31). The basic carboxy-terminal region of TFPI also contributes to high-affinity binding of factor Xa (32,33). While the inhibition of factor VIIa/TF by physiological concentrations of TFPI is dependent on initial binding to factor Xa, TFPI at 50-fold greater concentration can inhibit factor VIIa/TF in the absence of factor Xa. The function of the third Kunitz-type domain of TFPI is not clear and its deletion has no significant effect on factor Xa or factor VIIa/TF inhibition (27,28).

The concentration of TFPI in the plasma is about 2 nM, or 68–82 ng/mL (the apparent molecular weight of TFPI in plasma ranging from 34–41 kD) (27,28). Over 90% of circulating TFPI is bound to the lipoproteins, LDL, HDL, and Lp(a). Platelets contain about 10% of TFPI in 1–5 the circulating blood and release TFPI upon aggregation initiated by thrombin and other agonists (34). Plasma TFPI concentrations increase 2 to 4-fold after infusion of heparin, presumably by displacement of TFPI from heparin sulfate or other glycosaminoglycans on the surface of endothelial cells (35,36). TFPI associated with the endothelium may be important in local regulation of coagulation and its release by heparin may contribute to systemic anticoagulation (37). Conversely, heparin (in the presence of calcium) enhances the inhibition of factor Xa by full-length and carboxy-terminus truncated TFPI (28).

The tissue distribution of TFPI has not been fully elucidated (38). By immunohistochemistry, TFPI was detected in one study in megakaryocytes and microvascular endothelium but not in the endothelium of large and medium-sized vessels (39). Others recently reported the presence of endothelial TFPI in normal and atherosclerotic arteries but detected no TFPI in the smooth muscle cells of the medial layer (40). The inventors were also unable to detect TFPI in the conditioned medium of cultured human VSMC (See discussion in "Examples" infra.)

Mice with inactivated TFPI gene are subject to intrauterine lethality as a result of bleeding due to disseminated intravascular coagulation (41). Therefore TFPI likely plays an indispensable role among the endogenous antithrombotic molecules. However, physiological concentrations of TFPI do not completely inhibit thrombin generation. After prothrombotic stimuli (such as gram-negative sepsis) activate the factor VIIa/TF complex, disseminated intravascular coagulation can occur, consistent with the ability of physiological TFPI levels to inhibit factor VIIa/TF-initiated thrombin generation only after some factor X activation and prothrombinase complex formation have occurred (28). In contrast, pharmacological concentrations of TFPI inhibit the TF/factor VIIa complex in Xa-independent fashion and were reported to prevent disseminated intravascular coagulation after gram-negative bacterial sepsis (42,43) and thrombus formation after vascular injury (44–46). Experimentally, systemic administration of TFPI accelerates pharmacological lysis of arterial thrombi (47,48) and attenuated neointima formation after percutaneous balloon angioplasty (49,50).

Expression of tissue factor is tightly regulated (17,18) because TF is the common membrane receptor involved in blood vessel formation (62), hemostasis, and thrombosis at sites of vessel injury, inflammation and atherosclerosis. In healthy vessels, TF is mainly present in the adventitial layer (51). In contrast, in atherosclerosis, TF is expressed in the medial smooth muscle cell layer and the intimal plaque as well (52). TF is also upregulated acutely by shear stress (53), oxygen-free radicals generated during post-ischemic reperfusion (54), balloon injury (55) and, in vitro, by lipopolysaccharide, phorbol ester, interleukin-1, tumor necrosis factor, and other cytokines (17,18,56–61). The increased TF burden in the atherosclerotic vessel wall not only heightens the thrombotic risk, but also contributes to other problems. Factor Xa and thrombin, activated in TF-initiated pathways, are potent mitogens for vascular smooth muscle cells (63–65) and thereby may promote formation of the fibrous cap and restenosis after arterial revascularization interventions. TF may also directly contribute to neointimal smooth muscle cell accumulation through chemotactic effects (66). Thrombin activates matrix metalloproteinases involved in intimal smooth muscle cell accumulation and plaque rupture (67,68) and, through P-selectin release (25) may promote accumulation of inflammatory cells contributing more TF to the atherosclerotic plaque. Thus, TF initiates pathways, which lead to atherosclerotic plaque instability, rupture, thrombosis and exuberant proliferative "repair" and may promote thrombosis, inflammation, and intimal proliferation after percutaneous revascularization interventions as well.

None of the known anti-thrombotic methods employ gene therapy to achieve local expression of an anti-thrombotic agent specifically targeting the tissue factor pathway of thrombin generation. What is needed is an alternative or superior anti-thrombotic agent that can provide its therapeutic effects without incurring hemorrhagic risk. It is also desirable to have such an agent that can provide vessel site-specific anti-thrombotic activity and deter or prevent restenosis after balloon-injury. A method employing such an agent should be able to provide long-term therapeutic effects without increasing hemorrhagic risk, and without the need for co-administering multiple drugs.

BRIEF SUMMARY OF THE INVENTION

An anti-thrombotic vector, its manner of making, and methods employing gene therapy to achieve local expression of a transgenic anti-thrombotic agent are provided by the present invention. The new vector and methods specifically target the tissue factor pathway of thrombin generation. The present invention provides for maintaining the presence of a therapeutic amount of human tissue factor pathway inhibitor (TFPI) for days in the injured arterial wall, allowing anti-thrombotic effects to occur without the hemorrhagic risk typically experienced with known anti-thrombotic agents and methods.

The gene therapy methods of the invention permit limiting of the expression of a therapeutic amount of TFPI to a specific at-risk site in a blood vessel, thereby providing anti-thrombotic action and may deter restenosis after such events as a balloon injury to the vessel.

Local expression of transgenic TFPI by the transformed vascular cells spares the systemic hemostatic system and avoids the associated bleeding risks.

Certain embodiments of the present invention provide a recombinant adenovirus vector If containing Ad.TFPI, or human tissue factor pathway inhibitor cDNA that is operatively linked to a human cytomegalovirus immediate early promotor/enhancer (CMVp/e) and to a simian leukemia virus polyadenylation site (SV40pA).

Some embodiments of the invention provide an anti-thrombotic agent comprising a recombinant adenoviral vector containing a human TFPI gene operatively linked to CMVp/e and SV40pA. Other embodiments provide an anti-thrombotic agent comprising a transduced VSMC containing a transgenic TFPI gene.

The present invention also provides a method of making the Ad.TFPI vector, and includes ligating a cDNA encoding human full-length tissue factor pathway inhibitor into the BamHI site of the polylinker of the pACCMVpLpA plasmid to form the pLpA.TFPI shuttle plasmid; co-transfecting mammalian cells in tissue culture with said shuttle plasmid and plasmid pJM17; culturing the transfected cells until viral cytopathic effects are apparent; harvesting Ad.TFPI viral stock from the tissue culture; innoculating monolayers of mammalian cells in tissue culture with aliquots of high titer Ad.TFPI viral stock; harvesting culture medium and cells upon appearance of cytopathic effects; and purifying recombinant virion particles containing Ad.TFPI.

Another method in accordance with the present invention provides for transducing vascular smooth muscle cells, such as human arteriolar VSMC, with the Ad.TFPI vector and thereby causing the transgenic TFPI to be expressed by the cells. In certain embodiments of the new anti-thrombotic agent, the method includes exposing vascular smooth muscle cells at a predetermined site in a blood vessel to the purified Ad.TFPI virion particles, whereby the new TFPI gene becomes expressed by the cells, making tissue factor pathway inhibitor directly available at or near the particular targeted vessel site. The level of expressed transgenic TFPI cDNA is such that the resulting TFPI level at, and/or in the immediate vicinity of the site, exceeds the normally occurring TFPI level produced by the non-transduced tissue at the same locale in the vessel, such that the expressed transgenic TFPI provides an anti-thrombotic effect on the targeted area.

The present invention also provides a method of producing hTFPI at a predetermined site in a blood vessel. This method includes exposing vascular smooth muscle cells at a particular site with a recombinant adenovirus vector containing a human tissue factor pathway inhibitor (TFPI) gene operatively linked to a human cytomegalovirus immediate early promotor/enhancer and a simian leukemia virus (SV40) polyadenylation site. The target site within the blood vessel may be identified using conventional methods, and the Ad.TFPI virions together with a pharmacologically acceptable carrier, introduced at the target site by injection or catheter. Preferably at least about $1 \times 10^6$ vascular smooth muscle cells are transduced so that a therapeutic level of TFPI is produced in the target area.

The methods of the invention make it possible to protect an "at risk" site by converting a predetermined section of blood vessel tissue into special transgenic tissue containing vascular smooth muscle cells that express the transgenic human tissue factor pathway inhibitor gene and deter thrombus formation at that site. Accordingly, certain embodiments of the present invention provide "self-treating" anti-thrombotic agents comprising a vascular smooth muscle cell, such as a human VSMC, producing transgenic human tissue factor pathway inhibitor.

Another method of the present invention provides for maintaining a therapeutic amount of human TFPI at a desired blood vessel site that includes transfecting at least $1 \times 10^6$ vascular smooth muscle cells at the site with Ad.TFPI such that the TFPI gene is stably integrated into the cellular genome and TFPI is produced for at least 3 days.

Still other embodiments of the present invention provide methods of deterring or preventing thrombosis deposition or of protecting a blood vessel site against thrombosis deposition. The methods include introducing a transgenic human tissue factor pathway inhibitor gene at a predetermined site. The site can be a part of, adjacent, near or in the vicinity of where a balloon catheter injury has occurred, an atherosclerotic region of an artery or a balloon catheter injured atherosclerotic area occurs, or an angioplasty site, arteriovenous shunt, endovascular graft, or the like occurs. The manner of introduction of the TFPI gene may include exposing the vascular smooth muscle cells to a human tissue factor pathway inhibitor (TFPI) gene operatively linked to a human cytomegalovirus immediate early promotor/ enhancer and a simian leukemia virus (SV40) polyadenylation site. Similar methods offer protection to the blood vessel site against chronic vascular stenosis and intimal hyperplasia.

Accordingly, the present invention also provides a method of treating a site in a mammalian blood vessel that is at risk for thrombotic deposition and/or restenosis comprising genetically altering vascular smooth muscle cells at a site in the vessel such that the VSMC express a transgenic human tissue factor pathway inhibitor gene. The target site may be an atherosclerotic artery site, a balloon catheter injured artery site, an angioplasty site, arteriovenous shunt or an endovascular graft, or any area subject to intimal hyperplasia. The manner of accomplishing this genetic alteration preferably includes exposing the smooth muscle cells to a human tissue factor pathway inhibitor (TFPI) gene operatively linked to a human cytomegalovirus immediate early promotor/enhancer and a simian leukemia virus (SV40) polyadenylation site.

A preferred method of treating an "at risk" site in a mammalian blood vessel obtains genetic alteration of the target VSMC by first preparing a suitable vector. This includes ligating a cDNA encoding human full-length tissue factor pathway inhibitor into the BamHI site of the polylinker of the pACCMVpLpA plasmid to form the pLpA.TFPI shuttle plasmid. Mammalian cells in tissue culture are then co-transfected with the shuttle plasmid and plasmid pJM17, as described above. The transfected cells are then cultured until viral cytopathic effects appear, at which point Ad.TFPI viral stock is harvested from the tissue culture medium. Monolayers of mammalian cells in tissue culture are then innoculated with aliquots of high titer Ad.TFPI viral stock and the culture medium and cells are harvested after cytopathic effects appear, and the recombinant virion particles containing Ad.TFPI are purified. At least $1 \times 10^6$ vascular smooth muscle cells located at a predetermined site in a blood vessel are then infected with the purified Ad.TFPI virion particles, and the resulting transduced vascular smooth muscle cells subsequently begin producing a therapeutic amount of hTFPI.

These and other objects, features and advantages of the present invention will become apparent with reference to the following description and drawings.

BRIEF DESCRIPTION OF THE SEVERAL VIEWS OF THE DRAWING

The file of this patent contains at least one drawing executed in color. Copies of this patent with color drawing(s) will be provided by the Patent and Trademark Office upon request and payment of the necessary fee.

For a detailed description of a preferred embodiment of the invention, reference will now be made to the accompanying drawings wherein.

DETAILED DESCRIPTION OF THE INVENTION

Figure 1:
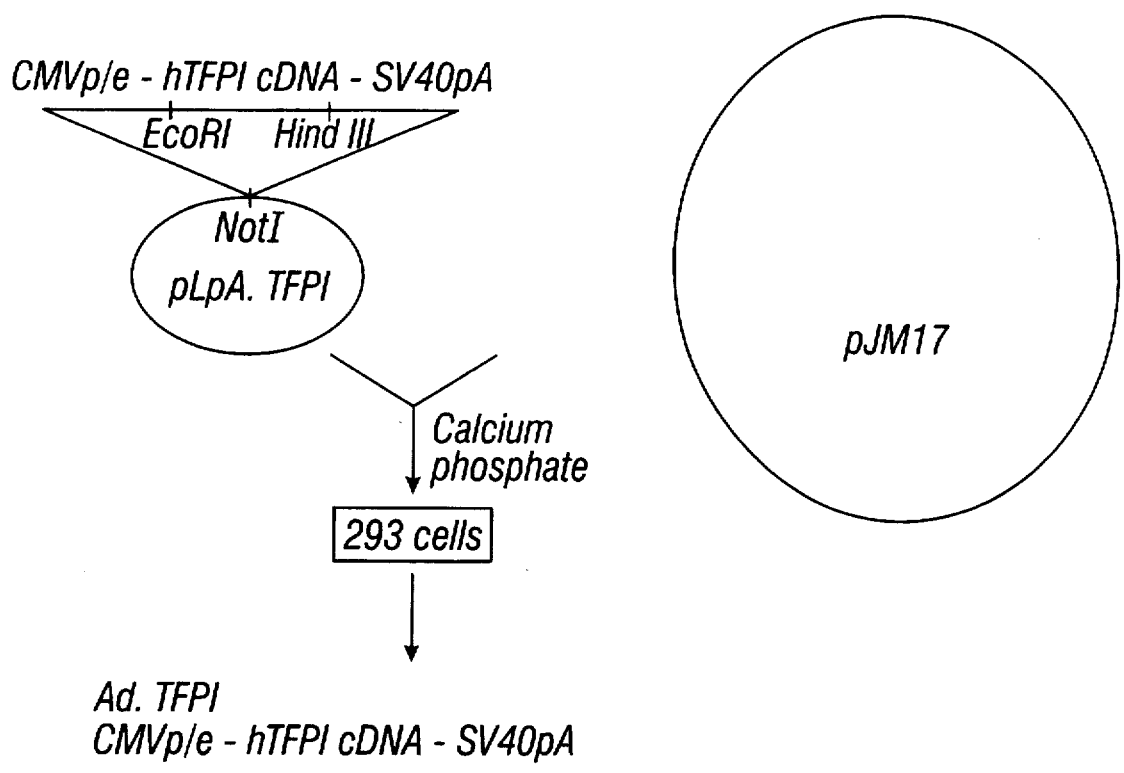
FIG. 1 shows the Ad.TFPI expression vector construct.

In accordance with the present invention, a recombinant replication-deficient adenovirus carrying the gene encoding recombinant tissue factor pathway inhibitor (TFPI) has been constructed, and it has been demonstrated that the viral construct has antithrombotic properties in in vitro tests and in animal models accepted by those of skill in the art of antithrombotics to be predictive of antithrombotic efficacy. The disclosed TFPI vector and methods not only establish the feasibility of genetic anticoagulant therapy, but also establish a practicable way of transferring anticoagulant therapy inhibiting tissue factor and thrombin activation from the circulating blood to the injured target wall via gene therapy. By achieving these two goals, the present invention overcomes conceptually and practically, by genetic means, two major limitations of standard pharmacological anticoagulation therapies: the need for multiple drug administration and systemic distribution of the anticoagulant drug. Some of the advantages of the present invention are that a) single administration of the new anticoagulant agent (Ad.TFPI) provides prolonged anticoagulant action (which no conventional drug presently achieves), and b) use of transduced TFPI shifts the presence of the anticoagulant from the circulating (systemic) blood into the wall of the vascular segment in need, thereby eliminating the cause of bleeding risk associated with systemic anticoagulant therapies. Due to local delivery, concentrations of TFPI in the blood stream are extremely low (eliminating systemic side effects), yet sufficiently high locally to exert anti-thrombic action.

The methods and compositions of the present invention provide a way to achieve gene transfer of TFPI into normal and atherosclerotic vessel walls. This is believed to be the first report of a gene therapy vector and method directed against tissue factor, factor VIIa, Xa and thrombin by TFPI gene transfer, and capable of exerting its effect locally at an at-risk site in a blood vessel.

While earlier studies have shown that tissue factor, the prothrombinase complex, and thrombin play pivotal roles in, respectively, initiating, amplifying, and precipitating thrombotic disease, it was unknown to attempt thrombotic protection using TFPI gene therapy. Also, in light of the fact that short-term (1–3 days) prevention of thrombin activity (5,6) or the platelet GP IIb/IIIa receptor blockers (13) has been proven to be unlikely to prevent the restenosis consistently, and further considering that thrombin generation in vivo appears to be unaffected by the presence of antithrombins tested in trials (7,8,69), it was not known whether sustained levels of antithrombin would be useful in vivo.

The present investigations, discussed in the "Examples" that follow, show how the local gene transfer of TFPI, a natural inhibitor of the coagulation protease complex factor VIIa/tissue factor and of activated factor X (factor Xa) is employed to prevent thrombus deposition and chronic vascular stenosis in blood vessels (arteries, veins, arteriovenous shunts, and endovascular grafts) by preventing tissue factor, factor Xa-, and thrombin-dependent mechanisms of recurrent thrombosis and intimal hyperplasia. The present invention demonstrates that tissue factor-dependent thrombosis, in particular, can be attenuated by local TFPI gene transfer. As discussed in greater detail in the examples which follow, a recombinant adenoviral vector encoding the TFPI gene was constructed, and it was demonstrated in animal models that vascular gene transfer of TFPI can be achieved. The mammalian models included dog vascular smooth muscle cells in tissue culture, balloon-injured normal dog femoral artery, atherosclerotic balloon-injured dog femoral artery, atherosclerotic rabbit carotid artery, pig carotid artery angioplasty, and human arteriolar smooth muscle cells in tissue culture.

TFPI expression was measured by ELISA in the conditioned medium of dog vascular smooth muscle cells (VSMC) infected with Ad.TFPI at a multiplicity of infection (MOI) of 500. For the purposes of this disclosure, multiplicity of infection (MOI) means the number of infectious virions per cell. Secretion of TFPI peaked after four days and was at a significant level after seven days post infection. The secreted TFPI was, on a molar basis, >90% active in inhibiting tissue factor/factor VIIa-initiated X activation, whereas control Ad (the same adenovirus vector minus the TFPI gene) did not induce expression of TFPI in dog VSMC. In similar studies using human VSMC in tissue culture, the inventor detected no TFPI in the uninfected human VSMC, but was present in generous amounts three days after infection with Ad.TFPI.

A brief overview of the methods employed in the animal models, and the results obtained, is as follows. Expressed transgenic TFPI was visualized by immunohistochemical staining four days after Ad.TFPI infection of cultured dog VSMC, balloon-injured dog femoral arteries and atherosclerotic Watanabe rabbit carotid arteries. After adenoviral-mediated transfer of the TFPI gene to balloon-injured carotid arteries in pigs, protection against thrombosis was observed, documented by continuous monitoring of carotid flow for 10 days after balloon injury. Briefly described, this procedure involved administration of Ad.TFPI ($5 \times 10^{10}$ pfu/mL) by local dwell to balloon-injured carotid arteries of micropigs (8 mm×2 cm balloon, 5 inflations to 6 atm). The injured arteries were stenosed by constrictors as further thrombogenic challenge. Intravenous heparin was given for up to 36 hours to protect the vessel until a biologically active level of gene expression was achieved, but no aspirin was given at any time. Carotid flow was continuously measured for 10 days by Doppler flow probe after balloon angioplasty and application of a constrictor to the injured arterial segment immediately following injury. Of 5 pigs that did not irreversibly occlude their carotid arteries within 36 h after surgery, 4 had no cyclic flow variations until day 10, while one animal suddenly occluded on day 7. In contrast, 8/9 pigs, given intraoperative heparin and daily aspirin after carotid angioplasty, developed severe, recurrent flow variations between day 3 and 10. No bleeding was observed, despite complete freedom from recurrent thrombus deposition in 4/5 pigs. These early investigations in animal models establish that local administration of a vector encoding TFPI in blood vessels is protective against thrombosis and diminishes the risk of systemic hemorrhage.

The following examples are offered by way of illustration and are not intended to limit the scope of the invention in any manner. All of the materials used in these examples were obtained from well known commercial sources, or as specifically stated in the examples.

EXAMPLE 1

Construction of a Replication-Deficient Adenovirus Encoding a Full Length Human Tissue Factor Pathway Inhibitor cDNA (Ad.TFPI)

To determine whether local vascular expression of human tissue factor pathway inhibitor (TFPI) might be protective against thrombosis, a recombinant adenovirus (Ad) carrying a cDNA encoding human TFPI was constructed (Ad.TFPI). The inventors took advantage of the high transduction ability of recombinant adenoviral vectors and constructed an adenovirus carrying the cDNA encoding TFPI, hereinafter referred to as "Ad.TFPI" In order to evaluate their hypothesis that local vascular expression of human TFPI is protective against thrombosis and restenosis of balloon-injured arteries.

Construction of an Adenoviral Shuttle Plasmid Carrying a Human TFPI cDNA

The cDNA encoding human full-length TFPI (29), cloned into the Searle/Monsanto-owned pmon3360 plasmid vector, was a kind gift of Dr. Tze-Chein Wun, Searle/Monsanto Corporation, Chesterfield, Missouri. The TFPI cDNA was cut out from pmon3360 with BamHI and was ligated into the BamHI site of the polylinker of the pACCMVpLpA (72,73), a bacterial shuttle plasmid containing: a) E1(A+B) deleted sequences from the left end of human serotype 5 adenovirus, b) a NotI fragment containing (from 5' to 3') the human cytomegalovirus immediate early promotor/enhancer (abbreviated "CMVp/e"), the pUC19 polylinker (derived from plasmid pUC19), the simian leukemia virus (SV40) polyadenylation site, c) and the ampicillin resistance gene. FIG. 1 shows the shuttle plasmid pACCMVpLpA.hTFPI, hereinafter referred to as "pLpA.TFPI". pACCMVpLpA (ref) was a gift from Dr. Robert D. Gerard, then at the University of Texas Southwestern Medical School, Dallas and is a derivative of pAC described by Gluzman et al in 1982 (74). pAC was originally constructed by inserting a type 5 adenovirus fragment extending from the EcoRI linker at the left end of the viral genome to the HindIII site at map unit 17.0 [1 map unit, (mu)=360 nucleotides], with a deletion comprising E1A and most of E1B between the PvuII site at 1.4 MU and the BglII site at 9.1 mu (74). Thus, pAC and its derivatives retain the leftmost 454 nucleotides of the viral genome, containing the origin of replication, the signal for packaging of DNA into the mature virion, and the sequences encoding the structural polypeptide IX.

Construction of Recombinant Adenoviral Vector Encoding the Human TFPI Gene

To construct a recombinant adenovirus encoding the mature TFPI protein, the shuttle plasmid pACCMVpLpA carrying the TFPI cDNA (pLpA.TFPI) was co-transfected with plasmid pJM17 (75) into the human embryonic kidney cell line 293 (FIG. 1). The 293 cells are available from American-Type Tissue Culture (Rockville, Md.). Homologous recombination of pLpA.TFPI and pJM17 was performed using the calcium phosphate method (76). The rescue vector, pJM17, was a gift from Dr. Frank Graham, University of Hamilton, Ontario and is a circular plasmid that contains the entire 36 kb adenoviral genome plus an approximately 4 kb fragment carrying the tetracyclin and ampicillin resistance genes (75). pJM17 contains adenoviral sequences homologous to those in pAC-derived vectors (including pACCMVpLpA). Because the 40 kb genome of pJM17 exceeds the adenoviral package restraints, homologous recombination between the pJM17 and adenoviral shuttle vectors (such as pACCMVpLpA) results in recombinant virions only if accompanied by deletion of the tetracyclin-ampicillin resistance genes. Therefore, viral plaque formation derived from nonrecombinants is rare, and most of the virions generated by homologous recombination with pJM17 are recombinants containing the foreign gene.

Ten days after transfection of pLpA.TFPI and pJM17 into a monolayer of 293 cells, viral cytopathic effects (CPE) spread across the entire cell layer in the 10-cm culture dish. The conditioned cell culture medium and the lysed cells were harvested, centrifuged for 5 min at 1000× g and the clarified supernatant (containing virus) was used for performance of a plaque titration assay and then stored at −80° C. In brief, a monolayer of 293 cells was infected (for 12 hours) with the clarified lysate of the 293 cells co-infected with pLpA.TFPI and pJM17. After 12 hours, the lysate was removed and the cells overlaid with a 1:1 mixture of Noble Agar and 2× MEM (modified Eagle's medium). Within 10 days, viral plaques had formed and 10 plaques were transferred to a monolayer of 293 cells in a 12 well dish (2 wells were left uninfected as control). After the 293 cells in the 10 infected wells showed CPE, the lysate of each well was clarified by centrifugation and used for ELISA analysis of TFPI in the conditioned medium and for further plaque purification of the relevant viral clones.

To assay for the presence of TFPI, 50 pL of the clarified conditioned medium of the 12 wells were analyzed with a commercially available ELISA for human TFPI (American Diagnostica, Greenwich, Conn.). The lysate of all 10 infected wells was found to contain >10 ng/mL TFPI, while TFPI was below the detection threshold (0.65 ng/mL) in the conditioned medium of uninfected 293 cells. Ad.TFPI virus was further purified by two rounds of plaque purification and each generation was checked by ELISA for the presence of TFPI in the conditioned medium.

Large Scale Preparation of Ad.TFPI

Ad.TFPI was grown up in 293 cells. High titer adenovirus was prepared following a procedure described by Robert D. Gerard (72,73), which was modified to obtain a higher purity. Monolayers of 293 cells were infected with aliquots of viral stocks diluted in DMEM supplemented with 2% fetal bovine serum. After appearance of cytopathic effects, the medium and cells were harvested in 0.1% NP 40. Following removal of the cell debris by centrifugation for 20 min at 5000× g, the virus was precipitated in 0.5 vol of 20% PEG 8000 and 2.5 M NaCl at 4° C. for 1 hour, followed by centrifugation for 20 min at 22,000× g. Recombinant virions were treated for 1 hour at room temperature with benzonase (50 units/mL) to remove nonviral DNA and RNA. Recombinant virions were then concentrated by CsCl gradient centrifugation (density p=1.25/p=1.4). Modification from the previously published Robert Gerard protocol include the benzonase step and two additional overnight equilibrium centrifugations at 180,000× g at 4° C. in CsCl at a density of p=1.34. Also, as a modification and to stabilize the virion particles, the recombinant virions were suspended in PBS containing sucrose (2% w/v), $MgCl_2$ (2 mM), and bovine serum albumin (0.1% w/v) (77). Finally, the virion particles were suspended in the PBS buffer and desalted by Sepharose CL4B (Pharmacia) chromatography.

Purified viral stocks were supplemented with 10% glycerol and stored at −80° C. The concentration of infectious viral particles was determined in 293 cells by plaque titration assay of serial dilutions of recombinant adenovirus from the frozen stock. Titers were routinely 101, plaque forming units (pfu)/mL. Titers were read when the number of plaques did not increase for three consecutive days (generally 7–10 days after infection of the 293 cell monolayers with dilutions of Ad.TFPI for 1 hour). The purity of Ad.TFPI was confirmed by the ability of individual plaques to induce TFPI secretion (measured by ELISA) into the conditioned medium of 293 cells. The identity of Ad.TFPI was further confirmed by PCR using the primers 5-AATCTTGCCCCTGCCCCTCTTA (SEQ ID NO: 1) (forward) and 5-AAACCATTCGGACCATCTTCACAA (reverse) (SEQ ID NO: 2). Ad.TFPI was only used for experiments, when TFPI was detected in the conditioned medium of all 8/8 wells of 293 cells infected with plaques from high-titer stock.

EXAMPLE 2

TFPI Gene Transfer in Vitro

Determination of TFPI Secreted by Dog VSMC in Vitro

Figure 2:
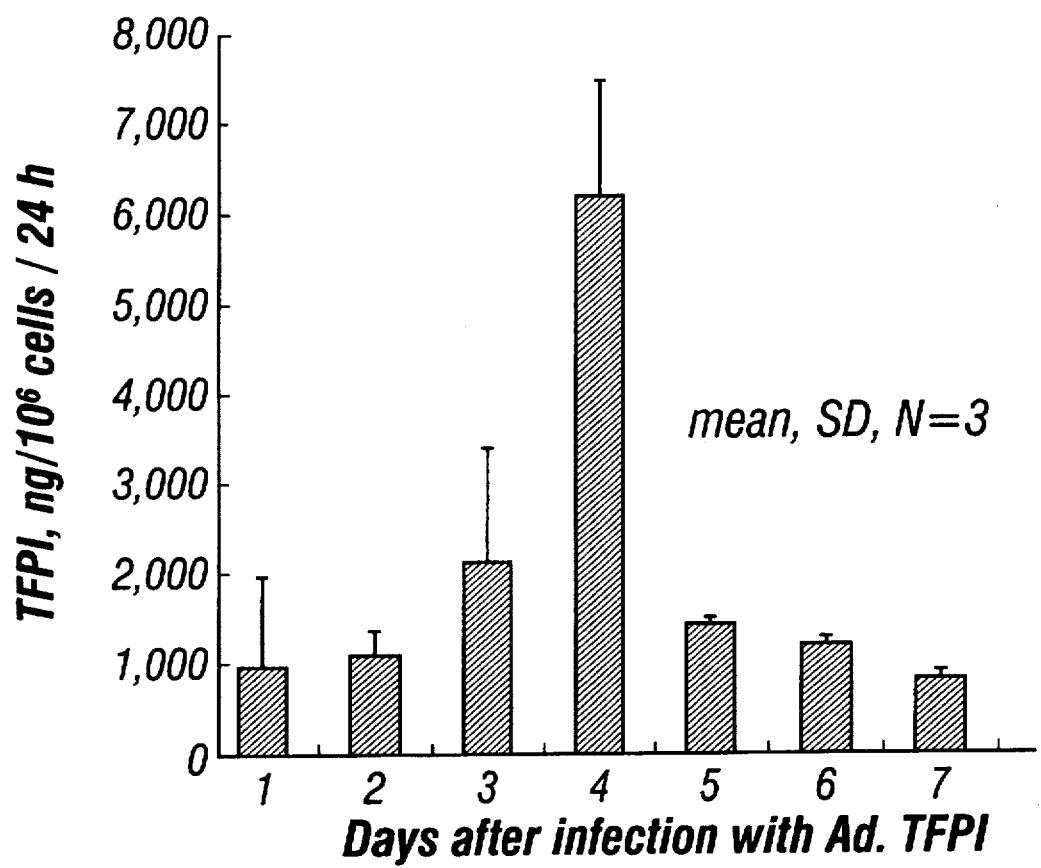
FIG. 2 is a graph showing the level of secretion of TFPI in dog vascular smooth muscle cells in vitro over a 7 day time course after infection with AD.TFPI.
Figure 3:
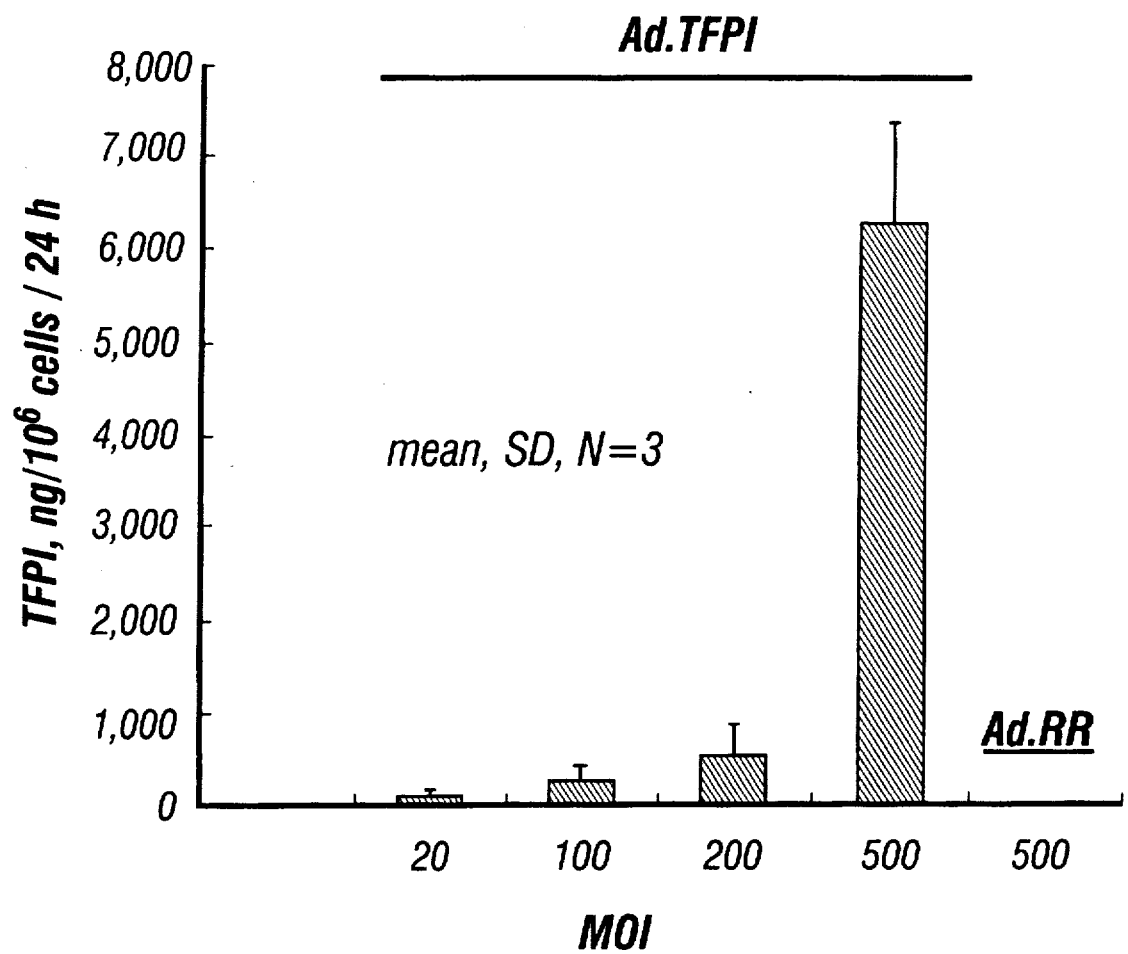
FIG. 3 is a graph showing the dose response of TFPI secretion in dog vascular smooth muscle cells in vitro infected with AD.TFPI at multiplicities of infection (MOI) of 20–500.
Figure 4:
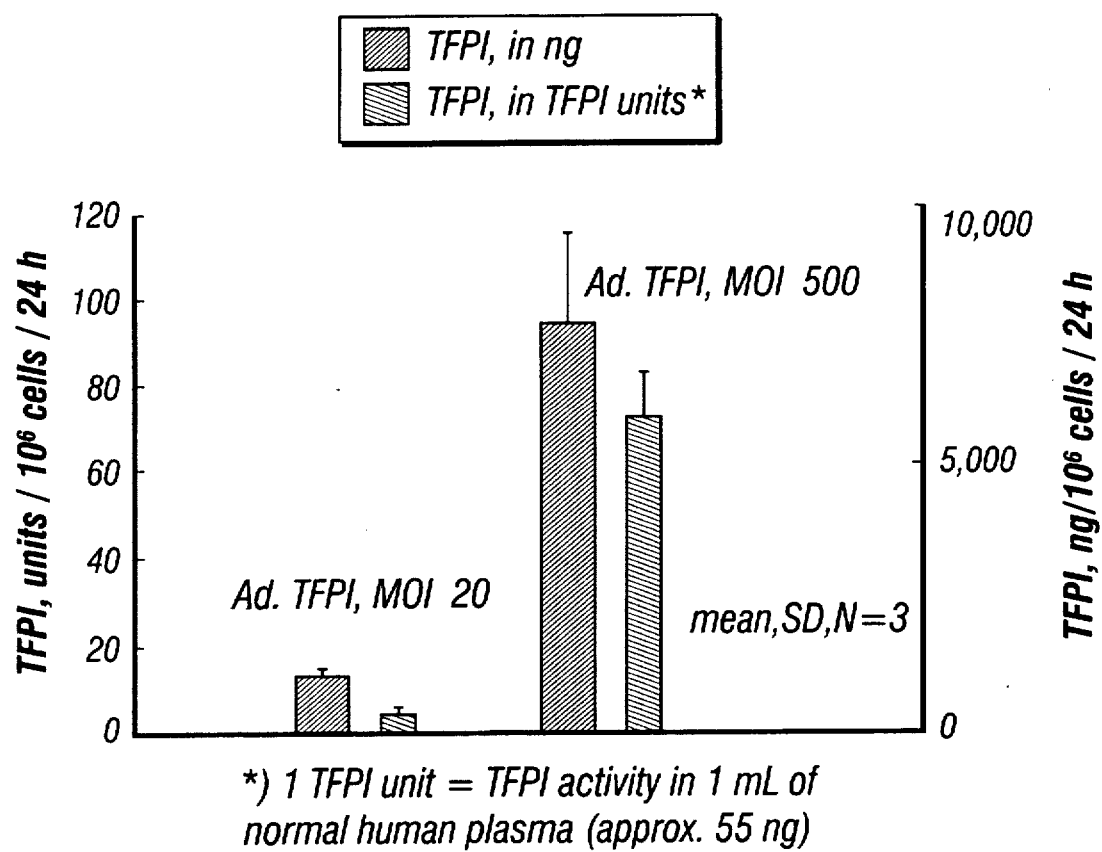
FIG. 4 is a graph showing mass vs. activity of TFPI secretion in dog vascular smooth muscle cells infected with AD.TFPI at multiplicities of infection (MOI) of 20 and 500.

FIGS. 2–4 show TFPI expression as measured by ELISA in the conditioned medium of dog vascular smooth muscle cells (VSMC) infected with Ad.TFPI at a multiplicity of infection (MOI) of 500. as described in detail below.

ELISA kits to measure TFPI secretion were purchased from American Diagnostica Inc., Greenwich, Conn. This ELISA (Imubind Total TFPI ELISA kit, product #849) is a sandwich ELISA, which consists of plates coated with a capturing rabbit anti-human polyclonal antibody, use of a biotinylated monoclonal antibody specific for the first Kunitz-like of TFPI domain, and streptavidin conjugated horseradish peroxidase complexes. Antibody binding is visualized by addition of the substrate, TMB. The detection threshold for TFPI in this ELISA is 0.36 ng/mL. The manufacturer's instructions were closely followed in the performance of the ELISA.

Dog vascular smooth muscle cells (dog VSMC) were explanted from femoral arteries as described (15) and transferred after 2 passages into 6-well polystyrene plates. For Ad.TFPI, the inventors studied multiplicities of infection (infectious virions/cell, MOI) of 20, 100, 200 and 500. Ad.RR was used at MOI 500 only. VSMC were infected for 6 hours with Ad.TFPI or Ad.RR (identical recombinant adenovirus as Ad.TFPI but without transgene), suspended in Dulbecco's modified Eagle medium (DMEM) with 2% fetal bovine serum. After 6 hours, the virus was removed and the cells were washed twice with DMEM supplemented with 2% fetal bovine serum (FBS) and hence cultured for additional 7 days in DMEM with 2% FBS.

Beginning the next day (24 hours after the start of the 6 hour infection), the conditioned cell culture medium was harvested, and stored at −80° C. (3 aliquots/well). The medium was collected daily and replaced by fresh culture medium for 7 days. Additional wells were infected in triplicate with Ad.TFPI at identical MOI and counted daily with a Coulter Counter (Model Z1) to allow expression of secreted TFPI in ng/$10^6$ cells/24 hours. TFPI was measured by ELISA in the conditioned medium of dog vascular smooth muscle cells (VSMC) infected with Ad. TFPI at a multiplicity of infection (MOI) of 500.

The daily secretion of TFPI by Ad.TFPI-infected dog VSMC is shown in FIG. 2 (MOI 500) and demonstrates the ability of VSMC to express human TFPI after gene transfer. Secretion of TFPI peaked on day 4, where it reached 5 µg/$10^6$ cells, and remained close to 700 ng/$10^6$ cells when last measured on day 7. No TFPI was detected in Ad.RR infected cells (data not shown). To see whether there was a virus-gene/dose relationship, dog VSMC were infected with Ad.TFPI at increasing MOI and TFPI accumulating during 24 hours was measured on day 4. Ad.RR at MOI of 500 was used as control. Secretion of TFPI (ng/$10^6$ cells/24 h) was 974±1,003 mean±SD) after one day, 6,145±1,125 after four days (peak), and 826±77 after seven days. Control Ad (no transgene) did not induce expression of TFPI in dog VSMC.

As shown in FIG. 3, the amount of TFPI secreted showed a direct relationship to the MOI used, although this relationship did not appear to be linear.

Determination of Anti-Factor VIIa/TF Activity of Secreted TFPI by Cultured Dog Vascular Smooth Muscle Cells The unique physiological aspect of TFPI is its factor Xa-dependent inhibition of the TF/factor VIIa enzyme complex. The most reliable assays for identifying TFPI are assays which measure this activity. Alternatively, TFPI can be measured by its ability to inhibit factor Xa activity directly in specific chromogenic inhibition assays. However, these direct factor Xa inhibition assays do not discriminate TFPI from other factor Xa inhibitors and are not useful when TFPI activity is measured in plasma or in other complex mixtures (27,28). Therefore, the inventors measured the activity of dog VSMC-secreted TFPI in a factor VIIa/ inhibition assay, where the factor VIIa/TF activity remaining after addition of TFPI is assayed by its ability to convert factor X to Xa, as measured by cleavage of a specific chromogenic substrate (SPECTROZYME Fxa, American Diagnostica) to release the chromophore p-nitroaniline. This assay was performed using a commercial kit (ACTICHROME TFPI Assay, American Diagnostica, Greenwich, Conn.) according to the manufacturer's instructions. In this assay, factor Xa is activated by a mixture of factor VIIa and TF and TFPI is expressed as units/mL. One unit of TFPI activity is defined as the activity of TFPI in 1 mL of human plasma (about 55 ng TFPI based on measurement in 300 volunteers).

TFPI activity was assayed in the conditioned medium of dog VSMC infected with the highest and lowest Ad.TFPI dose (MOI of 20 and 500). The medium harvested from the identical wells used in the TFPI ELISA were assayed for TFPI activity and read as TFPI activity (in units)/$10^6$ cells. (FIG. 4). When compared to a common human r-TFPI reference standard (a gift from Dr. Tze-Chein Wun, Searle/ Monsanto Corp., Chesterfield, Mo.) used in both the ELISA and the TFPI activity assay), the human TFPI secreted by dog VSMC was calculated to be 94% active on a molar basis. Control Ad (no transgene) did not induce expression of TFPI-related activity in dog VSMC in this assay.

Figure 5:
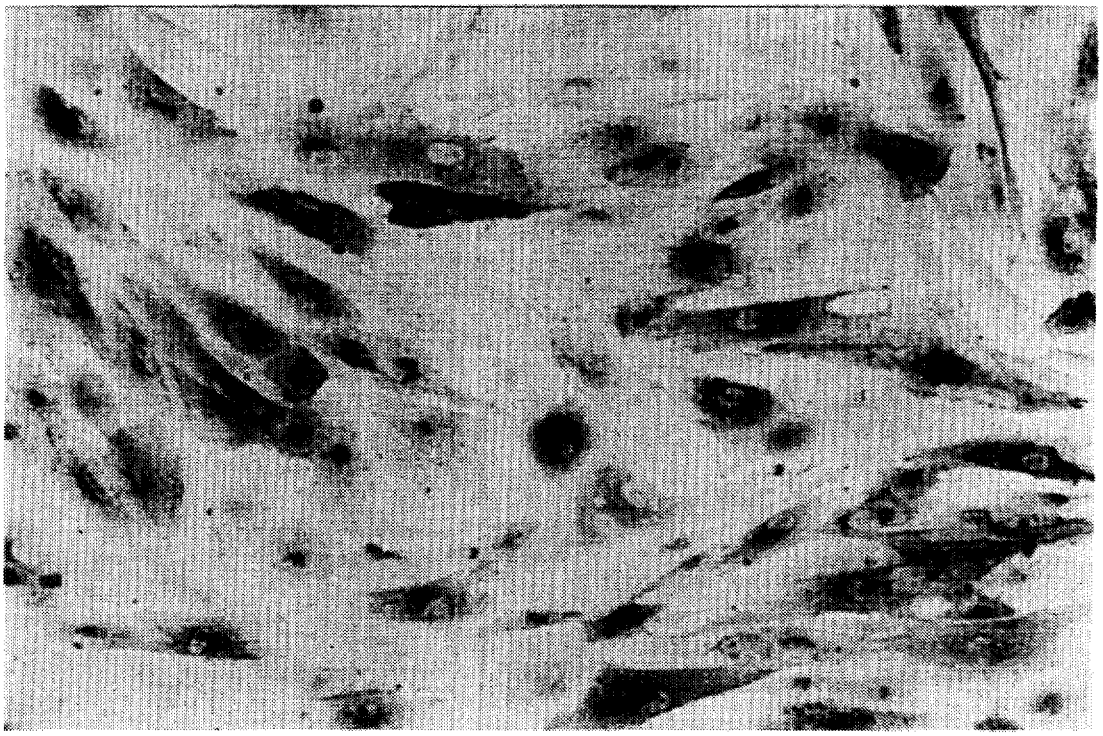
FIG. 5 is a color photograph of immunohistochemically stained dog smooth muscle cells in tissue culture, the dark brown color indicating expression of transgenic TFPI.

Detection of TFPI by Immunohistochemistry in Cultured Dog Vascular Smooth Muscle Cells For immunohistochemical detection of TFPI, a monoclonal antibody recognizing human TFPI was purchased from American Diagnostica, Greenwich, Conn. (Product # 4903). A standard procedure was followed for detection of TFPI in cultured vascular smooth muscle cells and arteries. For in vitro studies, chamber slides (Nunc) were seeded with dog VSMC and infected for 6 hours with Ad.TFPI or Ad.RR (identical virus without transgene) as control. After 6 hours, the virus was removed and the cells cultured for additional 4 days. Then, the cells were washed with PBS and fixed in with methanol for 20 min at room temperature, followed by exposure for 30 min to 2% horse serum in PBS. The cells were washed for 10 min in PBS, and incubated for 1 hour in either the monoclonal TFPI antibody provided by American Diagnostica (1:100) or a monoclonal antibody recognizing cytomegalovirus (Dako, 1:100) as negative control. Sections were washed for 10 minutes in PBS and subsequently exposed to a biotinylated horse antimouse antibody (Vector). After a washing step in PBS, the sections were incubated for 60 min in a suspension containing complexes of streptavidin-biotin-horseradish peroxidase (Vector). After two additional washing steps in PBS and water, antibody binding was visualized by exposure to DAB. The slides were counterstained for 30 min with methylene green. FIG. 5, shows cultured VSMC immunostained for TFPI, the brown-stained areas indicating expressed TFPI.

TFPI Secretion In Human Arteriolar Smooth Muscle Cells In Vitro

Recently, Wilcox et al. reported in preliminary work that they detected TFPI in the endothelium of large and medium sized arteries but not in the media of arteries. (40). To investigate whether cultured human VSMC produce TFPI with and without TFPI gene transfer, human arteriolar smooth muscle cells (a gift from Timothy Scott-Burden/ Texas Heart Institute) were infected for 6 hours with Ad.T-FPI and with Ad.RR at MOI 100. After 6 hours, the virus was removed and the cells were cultured for four days in DMEM with 2% fetal bovine serum. After three days, the medium was replaced with fresh medium and assayed after 24 hours for the presence of TFPI. No TFPI was detected by ELISA (detection threshold 0.36 ng/mL) in the conditioned medium of uninfected human VSMC or in human VSMC infected with Ad.RR (no transgene). In contrast, TFPI secretion was 347±80 ng/$10^6$ cells/24 h three days after infection with Ad.TFPI at MOI 100. Because the antibody used to detect TFPI has been raised against human TFPI, it was concluded in this study that cultured human arteriolar smooth muscle cells do not produce detectable amounts of TFPI.

The observations described in these Examples suggest that vascular gene transfer of TFPI to vascular cells is feasible with the methods and vectors of the present invention and that they have promise for wide spread application as vasoprotective therapy. First-generation vectors, such as the vector constructed by the inventors, express a transgene typically for about 7–21 days (70,71). The above examples describe the construction of a recombinant replication-deficient adenovirus carrying the gene encoding recombinant tissue factor pathway inhibitor (TFPI), and describe studies suggesting that the TFPI viral construct has anti-thrombotic properties. These examples show that human cultured VSMC do not secrete TFPI, and that both human and canine vascular smooth muscle cells can be transduced with TFPI to produce generous amounts of TFPI in gene (virus) dose-dependent fashion.

EXAMPLE 3

In Vivo Gene Transfer of TFPI

Figure 6:
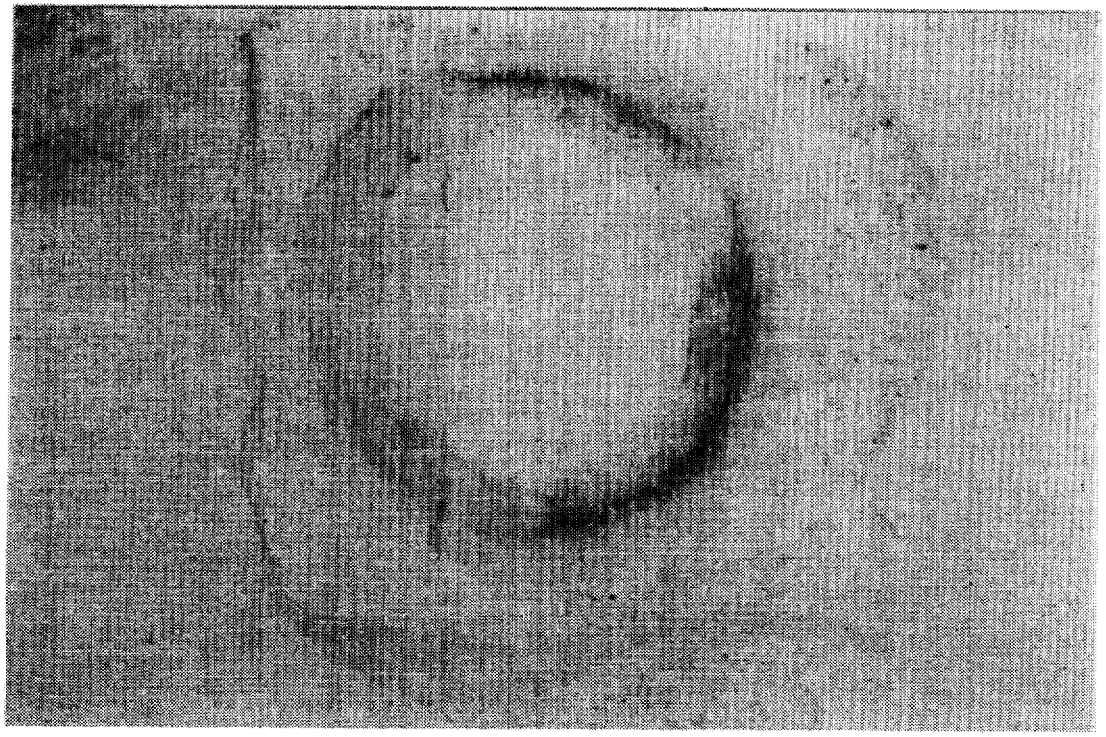
FIG. 6 is a color photograph of a dog femoral arterial wall, the dark brown color indicating immunohistochemical staining of balloon injured smooth muscle cells expressing TPFI.

Adenovirus-Mediated Gene Transfer Of TFPI to Balloon-Injured Normal Dog Femoral Artery Animal surgery was performed at the University of Texas Health Science Center at Houston Center for Experimental Surgery following Institutional guidelines. A 27-kg foxhound was sedated and anesthetized with isoflourane in oxygen. Following induction of anesthesia, a femoral cutdown was performed and a 5-F peripheral balloon angioplasty catheter (Meditech, balloon: 2 cm×7 mm was introduced through a femoral sheath placed into the distal femoral arteriotomy. The angioplasty catheter was advanced in retrograde fashion into the more proximal superficial femoral artery. Five min before peripheral balloon angioplasty (PTA), 200 units/kg of heparin were given, followed by five balloon inflations to 5 atm (30 sec inflation, 1 minute interval). After balloon dilation of the femoral artery, a gauge-22 catheter was introduced through a side branch into the balloon-injured segment and the segment was isolated by placement of temporary ligatures and rinsed with heparin/ saline to clear. Then, 700 μL of Ad.TFPI, $5.5\times10^{10}$ pfu/mL ($3.8\times10^{10}$ pfu) were instilled into the PTA-injured arterial segment. The virus was kept under slight pressure (0.5 atm) by infusion of saline. After 30 min, the Ad.TFPI was removed and the catheter was withdrawn through the side branch. The distal arteriotomy site was repaired and the animal allowed to survive for 4 days. Dogs were killed with pentobarbital overdose and arteries were sectioned and frozen in cryoprotective (O.C.T., 1:0 Miles) and the frozen blocks were transferred to −80° C. Prior to immunostaining, 5 μM sections were prepared and allowed to equilibrate in PBS. Then, the sections were exposed for 30 min in 2% horse serum in PBS, followed by incubation in room temperature of the sections for 30 min in 0.3% $H_2O_2$ in methanol. The sections were then stained for the presence of human TFPI as outlined in Example 2, describing detection of TFPI by immunohistochemistry in cultured dog VSM cells. A section from the balloon-injured artery infected with Ad.TFPI is shown in FIG. 6, showing the dog femoral artery section stained with TFPI (dark brown color).

TFPI Gene Transfer Into Atherosclerotic Rabbit Carotid Arteries

The ability to transfer foreign genes into atherosclerotic arteries is critical for the success of vascular gene therapy. A preferred gene therapy strategy in accordance with the present invention includes gene transfer to the uninjured atherosclerotic vessel several days before percutaneous revascularization interventions in order to enable high levels of foreign gene expression at the time of injury (based on the observation that adenoviral-driven gene expression typically requires 2–3 days to reach its peak). Preferably, the adenoviral vector is delivered at the time of percutaneous revascularization intervention and pharmacological antithrombotic protection given for the first 24–36 hours after the revascularization interventions.

Figure 7A:
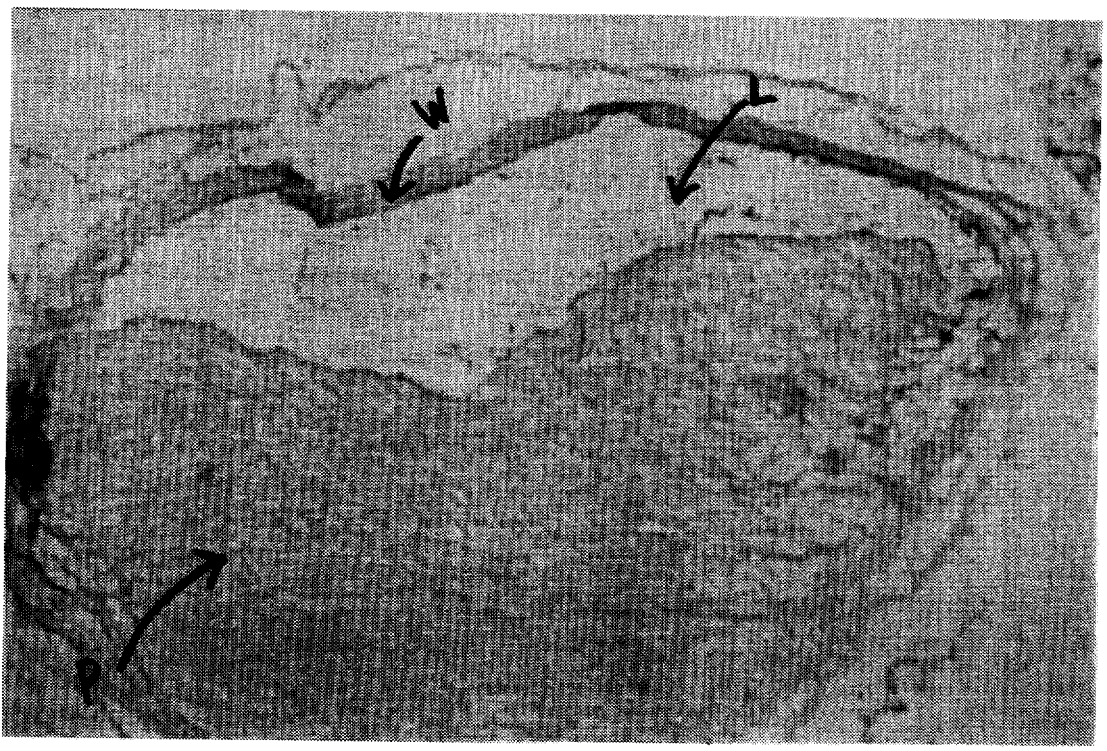
FIG. 7A is a color photograph showing, at 25× magnification, a section of an atherosclerotic rabbit carotid artery transduced with Ad.TFPI.
Figure 7B:
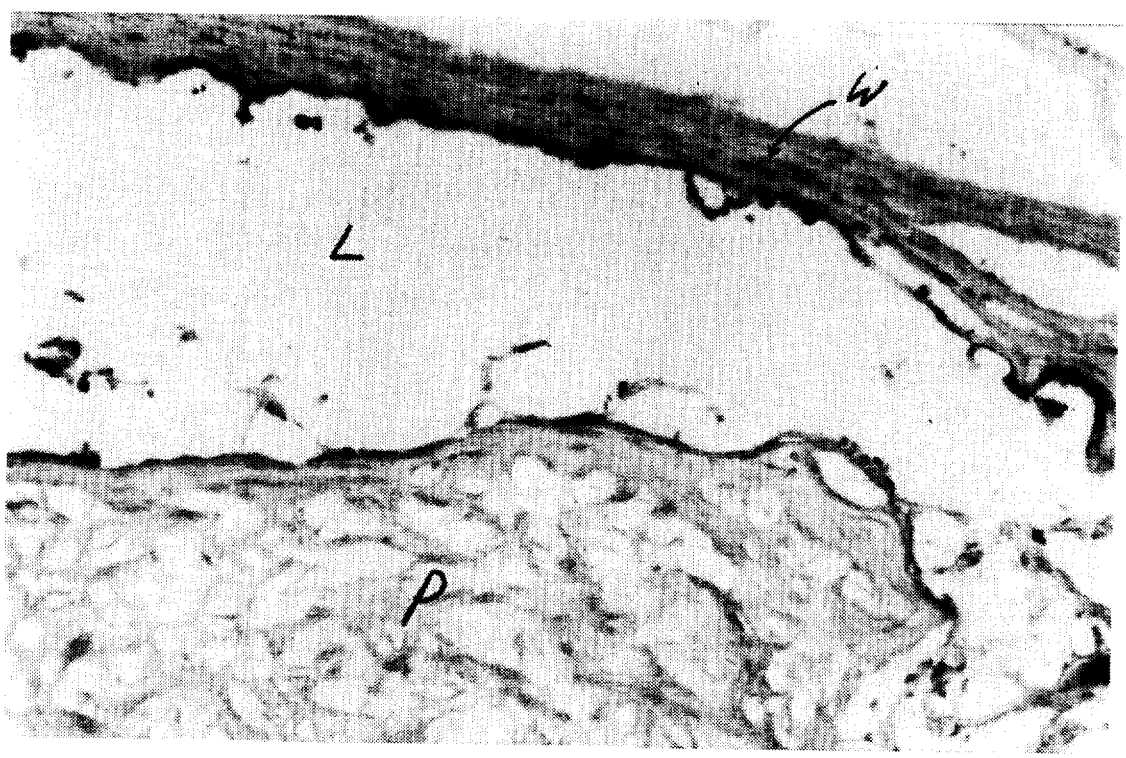
FIG. 7B is a detailed view, at 200× magnification, of the section shown in FIG. 7A.

The feasibility of gene transfer of TFPI to atherosclerotic arteries was first evaluated in the carotid artery of Watanabe rabbits not subjected to balloon injury. Rabbit experiments were performed at the University of Texas Health Science Center at Houston Center for Experimental Surgery following Institutional guidelines. At the time of surgery, three 28–36 months old hypercholesterolemic Watanabe rabbits were sedated with xylazine-ketamine, underwent endotracheal intubation, followed by induction of anesthesia with isofluorane. A carotid cut-down was performed and a gauge-22 catheter introduced through a distal arteriotomy site in the more proximal common carotid artery. An approximately 1 cm segment was temporarily isolated with silk sutures and filled with 300 μL of Ad.TFPI, $3 \times 10^9 – 1 \times 10^{10}$ pfu/mL. The virus suspension was allowed to dwell in the isolated segment for 30 min and was then removed, followed by arteriotomy repair and re-establishment of carotid flow. After closing the carotid cut-down wound, the animals were allowed to recover and were sacrificed (without administration of heparin) 4 days after surgery. Sections of the carotid artery were frozen in a cryoprotective agent (OCT, Miles Laboratories) and microscopic sections were prepared as described above for immunostaining with an antibody for human TFPI. One section of an atherosclerotic rabbit carotid artery transduced with 300 μL of Ad.TFPI, $1 \times 10^{10}$ pfu/mL, is shown in FIGS. 7A and 7B. FIG. 7A shows the artery at 25 fold magnification, and FIG. 7B is a detailed view (at 200 fold magnification) of a portion of the section shown in FIG. 7A. A large calcified atherosclerotic plaque (blue green color) is indicated by the arrow labeled "P", with the remaining lumen indicated as "L." TFPI that was transferred by Ad.TFPI into the artherosclerotic rabbit carotid artery was detected by immunostaining for human TFPI, and is indicated by the dark brown color in the strip of relatively normal arterial wall (arrow labeled "W"), opposite the atherosclerotic plaque.

Figure 8:
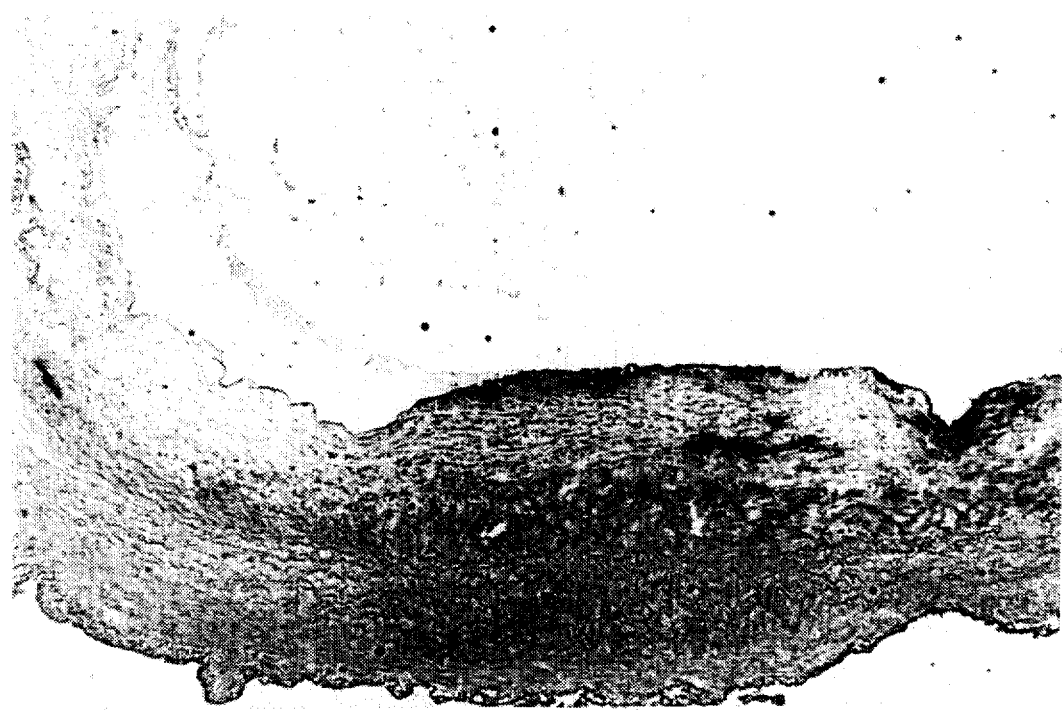
FIG. 8 shows TFPI (in brown) in the balloon injured, Ad.TFPI-treated atherosclerotic artery of a hypercholesterolemic dog. The animal was sacrificed and the artery stained for TFPI 4 days after balloon injury and local administration of Ad.TFPI for 30 min.

Adenovirus-Mediated TFPI Gene Transfer to an Atherosclerotic Balloon-Injured Dog Femoral Artery TFPI gene transfer was evaluated in a 24-month, severely hypercholesterolemic fox hound (peak total cholesterol, 1,626 mg/dL), that had received a 4% cholesterol diet for 6 month. The dog was sedated and anesthetized with intravenous pentobarbital (35 mg/kg), intubated, and ventilated with room air. After carotid cut-down, bilateral distal femoral cut-down was performed. An angioplasty catheter (Meditech, 7 mm×20 mm) was advanced sequentially into the more proximal femoral artery. After the administration of 200 units/kg of heparin, balloon angioplasty was performed in both femoral arteries with a 5×30-sec inflations to 5 atm (1 min interval between each inflation). Hence, a gauge-22 catheter was introduced through a side branch and advanced to the balloon-injured sites, which were temporarily isolated with silk sutures and dwelled with 500 μL of Ad.TFPI, $6 \times 10^{10}$ pfu/mL and Ad.COX-1, respectively. The virus suspension was allowed to dwell in the isolated segment for 30 min and was then removed. The side branch was tied off, followed by femoral arteriotomy repair and re-establishment of flow. After closing the cut-down wound in 3 layers, the animal was allowed to recover and was sacrificed (without administration of heparin) 4 days after balloon injury. The femoral arteries were frozen in an cryoprotective agent (OCT) and sections were prepared for immunostaining with an antibody for human TFPI, as described above. Transgenic TFPI (in brown) is seen in the atherosclerotic plaque in FIG. 8.

Antithrombotic Effect Of TFPI Gene Transfer In A Pig Carotid Angioplasty Model

Pig experiments were performed at the University of Texas Health Science Center at Houston Center for Experimental Surgery following Institutional guidelines. The transfemoral porcine carotid artery balloon angioplasty model has been previously described (76), the disclosure of which is incorporated herein by reference. Yukatan micropigs (weight 20–25 kg) were sedated with xylazine and ketamine, followed by induction of anesthesia with isoflourane in oxygen. A right femoral cut-down was performed and an 8F sheath was introduced into the femoral artery and flushed with saline. Transfemoral carotid angioplasty was performed by advancing an 8 mm×2 cm peripheral balloon angioplasty catheter (Meditech) to either carotid artery. Through an anterior cut-down in the neck, the ipsilateral internal jugular vein was cannulated to provide an infusion port for heparin for the first 3–6 hours as well as a port for blood drawls. Five minutes before carotid angioplasty, 200 units/kg of heparin were administered followed by five balloon inflations to 6 atm, with one minute interval between inflations. Following completion of carotid balloon angioplasty, a gauge-22 catheter was advanced through an arteriotomy into the injured arterial segment, which then was temporarily isolated by silk sutures proximal and distal to the site of injury. The isolated arterial segment was rinsed with saline to clear, followed by infusion and dwell of 800 μL of Ad.TFPI ($5.5 \times 10^{10}$ pfu/mL). The infusate was kept under approximately 0.5 atm of pressure for 30 minutes with an inflation device (Scimed). After 30 minutes, the virus suspension was removed. Flow was re-established by removing the temporary ligatures and arteriotomy repair. An additional bolus of heparin (100 units/kg) was given 5 min before reflow. A Doppler flow probe was applied at the proximal end of the balloon injured carotid segment. The animal was kept under observation for 2 hours, followed by application of a constrictor adjusted to reduce the blood flow to 50% compared to baseline. After closure of all wounds, the animal was allowed to recover in the surgery cages and the exteriorized Doppler flow probe cables were connected to the flow recorder. To prevent thrombosis before significant TFPI was expressed, the pigs received up to 36 hours of heparin (28±6.6 hours, range 24–36 hours), at 50–60 (52±4.5) units/kg/hour. After denudation by angioplasty, the smooth muscle cells are the main cell type to be exposed to the recombinant adenoviruses.

Carotid flow was monitored continuously by Doppler flow probe for 10 days.

Four pigs occluded within 48 hours of surgery and were excluded from further study. None of the 5 pigs surviving 48 hours without irreversibly carotid artery occlusion, showed cyclic flow variations thereafter, although 1 of the 5 occluded suddenly on day 7. The other 4 pigs showed no flow disturbance until day 10 and were allowed to survive for 28 days before sacrifice for evaluation of neointima formation in presently ongoing studies. No bleeding was observed after heparin withdrawal in the Ad.TFPI-treated pigs. In contrast, 8 of 9 micropigs, that had previously been studied, had received heparin and daily aspirin and shown severe cyclic flow reductions with irreversible occlusion in 5 of 9. In another carotid angioplasty study in domestic pigs, animals receiving local carotid Ad.LacZ (adenovirus carrying the gene encoding β-galactosidase) had shown hundreds of cyclic flow reductions, with irreversible occlusion occurring in 50% of pigs. Animals, which occluded irreversibly before day 3 had been excluded in that study as well (76).

By way of further comparison, in an actual balloon angioplasty micropig model identical to the one described above, 100 μg recombinant TFPI/min/Kg weight was given systemically to achieve antithrombosis protection. Severe bleeding at the surgical wound site and occasional pulmonary hemorrhage were observed at this dosage. In a 25 kg average weight pig, this dose approximates about 25000 μg TFPI per pig per hr, or about 600,000 μg TFPI over a 24 hr. period. In contrast, the in vitro data obtained in the present studies show that approximately $1 \times 10^6$ Ad.TFPI transfected vascular smooth muscle cells secrete approximately 6 fig TFPI in 24 hrs (FIG. 2). Transduction of an in vivo vessel area, containing about $1 \times 10^6$ VSM cells, is adequate to obtain localized antithrombotic activity. In any case, as with other antithrombotic drugs, one would determine empirically the precise titer of Ad.TFPI that will yield the desired level of expression. For example, a level of local TFPI production comparable to about 100 μg recombinantTFPI/min/Kg given systemically.

The above-described study in pigs was not preceded by dose-finding study, and thus, a more optimal gene (viral) dose may be obtainable. The dose chosen for testing was similar to that found previously effective in a study of cyclooxygenase-1 gene transfer in the same carotid angioplasty model (15). It should be also noted that, contrary to previous studies by the inventors, the present vectors used in the in vitro and in vivo studies were purified by 3 (rather than 1) CsCl centrifugation steps.

Additional conclusions from these studies are that TFPI gene transfer can be achieved in normal and atherosclerotic arteries in vivo and that gene transfer of TFPI into balloon angioplasty injured porcine carotid arteries results in reduction of cyclic flow variations, when compared to previous controls given aspirin. Indeed, 8 out of 9 balloon angioplasty-injured pigs had shown hundreds of cyclic flow variations beginning 2–4 days after surgery, despite daily administration of 325 mg aspirin (in addition to intra-operative heparin). In contrast, of the 5 Ad.TFPI pigs that had not occluded before day 3, none developed cyclic flow variations (CFV) between day 2 and day 10, although one animal suddenly occluded on day 7. One animal had began to develop CFV on day 2, but these faded within 24 hours (on day 3). This has not been previously observed, as frequency and severity of CFV in this model tend to increase (not decrease) in severity in the first week after balloon injury and application of constrictor (15).

The studies carried out in the course of developing the present invention indicate that the TF-initiated thrombin generation plays a pivotal role in thrombosis of balloon-injured carotid arteries and suggests that inhibiting TF by in situ generated TFPI is vasoprotective without hemorrhagic risk. Thus, TFPI gene therapy provides, among other useful applications, a new approach to test the thrombin hypothesis (i.e., that thrombin plays a pivotal role arterial in thrombogenesis). Because coagulant factors inhibited by TFPI (tissue factor, factor Xa, and thrombin) play a role in the generation of fibrin clots, in restenosis, and in venous thrombosis (where platelets play a minor role), TFPI gene transfer may be more effective than COX-1 transfer and have a broader range of action. COX-1 enhances the synthesis of prostacyclin, which inhibits platelets and relaxes the vessel wall. Because pharmacological levels of TFPI administered systemically shut off thrombin generation efficiently, as discussed in the Background of the Invention, the high levels of TFPI generated in vitro in VSMC after adenovirus-mediated TFPI gene transfer, in accordance with the present invention, indicate that the locally expressed TFPI will express TFPI for at least 7 days, silencing TF, factor VIIa, Xa and thrombin in the vessel wall and at the vessel wall/blood interface.

Ongoing investigations by the inventors includes biochemical studies of coagulation protease-inhibitor complexes in the vessel wall. The inventors anticipate that further work on the inhibition of TF, factor VIIa, Xa and thrombin by TFPI gene transfer, utilizing the methods disclosed herein, will extend the use of the present compositions to TFPI gene therapy for arteriovenous shunts, and venous and endovascular grafts.

From the present investigations, the inventors determined for the first time that local expression of the TFPI gene has vasoprotective effects with good potential for therapeutic use in blood vessels at thrombotic risk. Ongoing work by the inventors will assess the extent to which TFPI gene transfer exerts protection against intimal thickening and luminal narrowing (restenosis) after balloon injury. Effective prevention of restenosis in atherosclerotic arteries may require prolonged drug administration, including recombinant TFPI, until the first phase of endothelial healing is complete. A combined approach of local prevention of recoil, platelet activation, thrombin generation, and fibromuscular hyperplasia may provide the safest and most efficacious protection against recurrent subacute thrombosis and restenosis.

Importantly, the present invention of local TFPI gene therapy is also of value as an adjunct to other systemic therapies. As mentioned above in the Background of the Invention, in clinical trials studying heparin and the thrombin inhibitor, desirudin, in acute coronary syndromes, most patients who developed intracranial bleeds had received aspirin, heparin or desirudin, and a thrombolytic agent (1–3). Those trials indicated that systemic blockade of multiple platelet/coagulation pathways is not without risk. Similarly, high dose heparin is poorly tolerated in conjunction with potent platelet inhibition with c7E3 Fab (ReoPro). In contrast, local gene therapy with TFPI, in accordance with the present invention, is expected to enhance the efficacy and safety of aspirin and to permit use of lower doses of the IIb/IIIa receptor blockers, thereby sparing systemic fibrin formation, and thus reducing the hemorrhagic risk. This is of considerable importance because aspirin (inhibiting $TXA_2$ and collagen-induced platelet aggregation) is routinely given to patients undergoing percutaneous revascularization interventions.

REFERENCES

1. Antman E. for the TIMI-gA Investigators: Hirudin in myocardial infarction. Safety report from the thrombolysis and thrombin inhibition in myocardial infarction (TIMI-9A) trial. *Circulation* 1994;90: 1624–1630.

2. The Global Use of Strategies to Open Occluded Coronary Arteries (GUSTO) Iha Investigators. Randomized trial of intravenous heparin versus recombinant-hirudin for acute coronary syndromes. *Circulation* 1994; 90: 1631–1637.

3. Neuhaus K L, von Essen R, Tebbe U, et al: Safety observations from the pilot study of the randomized r-hirudin for improvement of thrombolysis (HIT-III) study. *Circulation* 1994;90:1638–1642.

4. EPIC investigators: Use of a monoclonal antibody directed against the platelet glycoprotein IIb/IIIa receptor in high-risk coronary angioplasty. *N Engl J Med* 1994;330:956–961.

4a. Meyer B J, Fernandez-Ortiz A, Mailhac A, Falk F, Badimon L, Michael A D, Chesebro J H, Fuster V, Badimon J J: Local delivery of r-hirudin by a double-balloon perfusion catheter prevents mural thrombosis and minimizes platelet deposition after angioplasty. *Circulation* 1994; 90:2474–80.

5. HELVETICA Investigators: A comparison of hirudin with heparin in the prevention of restenosis after coronary angioplasty. *N Engl J Med* 1995; 333:757–763.

6. Bittl J A, Strony J, Brinker J A et al for the Hirulog Angioplasty Study Investigators: Treatment with bivalirudin (Hirulog) as compared with heparin during coronary angioplasty for unstable angina. *N Engl J Med* 1995;333:764–769.

7. Zoldhelyi P, Bichier J, Owen W G, Grill D E, Fuster V, Mruk J S, Chesebro J H. Persistent thrombin generation during specific thrombin inhibition with hirudin. *Circulation* 1994;90:2671–2678.

8. Zoldhelyi P, Bichler J, Owen W G, McBane R, Hassinger N, Gaspar D, Chesebro J H. Measurement of thrombin-hirudin complex documents persistent thrombin formation in patients with unstable angina during anticoagulation with recombinant hirudin (Abstr.). *Circulation* 1993;88 (Suppl I) I-3 19.

9. Granger C B, Miller J M, Bovill E G, Gruber A, Tracy R P, Krucoff M W, Green C, Berrios F, Harrington R A, Ohman E M, et al: Rebound increase in thrombin generation and activity after cessation of intravenous heparin in patients with acute coronary syndromes. *Circulation* 1995; 91:1929–35.

10. Theroux P, Waters D, Lam J, Juneau M, McCans J: Reactivation of Unstable Angina After the Discontinuation of Heparin. *New Engl J Med* 1992; 327:141–145.

11. The IMPACT Investigators: Randomized placebo-controlled trial of effect of eptifibatide on complications of percutaneous coronary intervention: *Lancet* 1979; 359:1422–1428.

12. Topol E J, Califf R M, Weisman H F, Ellis S G, Tcheng J E, Worley S, Ivanhoe R, George B S, Fintel D, Weston M, Sigmon K, Anderson K M. Lee K L, Willerson J T, for the EPIC Investigators: Randomised trial of coronary intervention with antibody against platelet IIb/IIIa integrin for reduction of clinical restenosis: Results at six months. *Lancet* 1994, 343, 881–886.

13. Lincoff M A, for the EPILOG Investigators: Platelet glycoprotein IIb/IIIa receptor blockade and low-dose heparin during percutaneous coronary revascularization. *N Engl J Med* 1997;336: 1689–1896.

14. Lee S W, Trapnell B C, Rade J J, Virmani R, Dichek D A: In vivo adenoviral vector-mediated gene transfer into balloon-injured rat carotid arteries. *Circ. Res.* 1993; 73:797–807.

15. Zoldhelyi P, McNatt J, X -M Xu, Meidell R, Loose-Mitchell D, Willerson J T, Wu K K. Prevention of arterial thrombosis by adenovirus-mediated transfer of cyclooxygenase gene. *Circulation* 1996; 93:10–17.

16. Spriggs D, Gold H K, Hashimoto Y, Van Routte E, Vermylen J, Collen D: Absence of potentiation with murine antiplatelet GP IIb/IIIa antibody of thrombolysis with recombinant tissue-type plasminogen activator (rt-PA) in a canine venous thrombosis model. *Throm Haemost* 1989;61:93–96.

17. Edgington T S. Mackman N, Brand K, Ruf W: *Thromb Haemost* 1991;66:67–79.

18. Rapaport S I, Rao L V M: Initiation and regulation of tissue factor-dependent blood coagulation. *Arteriosclerosis and Thrombosis* 12(10): 1111–1121, 1992.

19. Martin D M A, Boys C W G, Ruf W: Tissue factor: molecular recognition and cofactor function. *FASEB J*, 1995; 9:852–859.

20. Miletich J P, Jackson C M, Majerus P W. Properties of the factor Xa binding site on human platelets. *J Biol Chem* 1978, 253:6908–6916

21. Bauer K A, Kass B L, ten Cate H, Hawiger J J, Rosenberg R D: Factor IX is activated in vivo by the tissue factor mechanism. *Blood* 1990; 76(4):731–736.

22. Nesheim M., and K G Mann: Thrombin-catalyzed activation of single-chain bovine factor V. *J. Biol. Chem* 1979;254: 1326–1334.

23. Hoyer L W and N C Trabold: Effect of thrombin on human factor VIII: cleavage of the factor procoagulant protein durino activation. *J. Lab. Clin. Med* 1981;97: 50–64.

24. Gailani D, Broze, Jr. G J: Factor XI activation in a revised model of blood coagulation. *Science* 1991;253: 909–912.

25. Sugama, Y., C. Tiruppathi, K. Janakidevi, T. T. Andersen, J. W. Fenton II, and A. B. Malik. 1992. Thrombin-induced expression of endothelial P-selectin and intercellular adhesion molecule-1: a mechanism for stabilizing neutrophil adhesion. *J. Cell. Biol.* 119(4):935–944.

26. Coller B S, Anderson K, Weisman H F: New antiplatelet agents: platelet GPIIb/IIIa antagonists. *Thromb Haemost.* 1995;74:302–308.

27. Girard T J, Broze Jr. G J.: Tissue factor pathway inhibitor. In: *Methods in Enzymology*, Academic Press 1993, Vol.222, pp 195–208.

28. Broze, Jr. G J: TFPI and the revised theory of coagulation. *Annu Rev Med* 1995;46: 103–112.

29. Wun T C, Kretzmer K K, Girard T J, Miletich J P, Broze G J: Cloning and characterization of a cDNA coding for the lipoprotein-associated coagulation inhibitor shows that it consists of three tandem Kunitz-type inhibitory domains. *J Biol Chem* 1988; 263:6001–6004.

30. Hoist J, Lindblad B, Nordfang 0, Ostergaard P B, Hedner U: Does glycosylation influence the experimental antithrombotic effect of a two-domain tissue factor pathway inhibitor. *Haemostasis* 1996; 26(1):23–30.

31. Van't Veer C & Mann K G: Regulation of tissue factor initiated thrombin generation by the stoichiometric inhibitors tissue factor pathway inhibitor, antithrombin III, and heparin co-factor II. *J Biol Chem* 1997;272:4367–4377.

32. Wesselschmidt R L, Girard T J, Likert K M, Wun T C, Broze G J Jr: Tissue factor pathway inhibitor: the carboxy-terminus is required for optimal inhibition of factor Xa. *Blood* 1992;79:2004–2010.

33. Higuchi D A, Wun T C, Likert K M, Broze Jr. G J: *Blood* 1992;79:1712

34. Novotny W F, Girard T J, Miletich J P, Broze Jr. G J: Platelets secrete a coagulation inhibitor functionally and antigencally similar to the lipoprotein-associated coagulation inhibitor (EPI). *Blood* 1988;72:2020–2025.

35. Sanset P M, Abildgaard U, Larsen M L: Heparin induces release of extrinsic coagulation pathway inhibitor (EPI). *Thromb Res* 1988;50:803–813.

36. Novotny W F, Brown S G, Miletich J P, et al: Plasma antigen levels of the lipoprotein-associated coagulation inhibitor in patient samples. *Blood* 78:387–393.

37. Hansen J -B, Sandset P M, Huseby K R, Huseby N -E, Nordey A: Depletion of intravascular pools of tissue factor pathway inhibitor (TFPI) during repeated or continuous intravenous infusion of heparin in man. *Thrombosis and Haemostasis* 1996;76:703–9.

38. Fleck R A, Rao L V M, Rapaport S I, Varki N: Localization of human tissue factor antigen by immunostaining with monospecific, polyclonal anti-human tissue factor antibody. *Thrombosis Research* 1990;57:765–781.

39. Werling R W, Zacharski L R, Kisiel W, Bajaj S P, Memoli V A, Rousseau S M: Distribution of tissue factor pathway inhibitor in normal and malignant human tissues. *Thrombosis and Haemostasis* 1993; 69(4): 366–369.

40. Wilcox, J N, Noguchi S, Ezban M, Wilcox, J N: Immunohistochemical localization of FVII, FX, TF, and TFPI in normal and atherosclerotic vessels. Microcirculation (Abstract) 1997; 4:191.

41. Broze, Jr. G J: Tissue factor pathway inhibitor (TFPI) gene disruption in mice produces intrauterine lethality. *Blood* 1997; 90:944.

42. Creasey A A, Chang A C, Feigen L, et al; Tissue factor pathway inhibitor reduces mortality from *E.coli* septic shock. *J Clin Invest* 1993; 91:2850–2856.

43. Carr C, Bud G S, Chang A C, Peer G T, Palmier M O, Frazier R B, Gustafson M E, Wun T C, Creasey A A, Hinshaw L B, et al: Recombinant *E. coli*-derived TFPI reduces coagulopathic and lethal effects in the baboon.

44. Lindahl A K, Nordfang 0, Wudgoose P, Kelly A B, Harker L A, Hanson S R: Antithrombotic effects of a truncated tissue factor pathway inhibitor (TFPI) in baboons. *Thromb Haemost* 1993;69:742 (Abstract).

45. Holst J, Lindblad B, Bergquist D, et al; Antithrombotic effect of a recombinant tissue factor pathway inhibitor (TFPII-161) in experimental venous thrombosis—a comparison with low-molecular weight heparin. *Thromb Haemost* 1994;71:214–219.

46. Ornberg R L, Deune E G, Ozbek M R, Wun T -C, Khouri R K: Localization of topically applied TFPI binding sites in an intimectomized microvessel. *Thrombosis and Haemostasis* 1995; 73(1):55–8.

47. Haskel E J, Torr S R, Day K C, et al: Prevention of arterial reocclusion after thrombolysis with recombinant lipoprotein-associated coagulation inhibitor. *Circulation* 1991;84: 821–827.

48. Abendschein D R, Meng Y Y, Torr-Brown S, Sobel B E: Maintenance of coronary patency after fibrinolysis with tissue factor pathway inhibitor. *Circulation* 1995;92(4):944–9.

49. Jang Y, Guzman L A, Lincoff M, Topol E J: Influence of blockade at specific levels of the coagulation cascade on restenosis in a rabbit atherosclerotic femoral artery injury model. *Circulation* 1995;92:3041–3050.

50. Oltrona L, Speidel C M, Reechia D, Abendsehein D R: Inhibition of tissue factor-mediated thrombosis markedly attenuates stenosis after balloon-induced arterial injury in hyperlipidemic minipigs. *Circulation* 1994; 90(4): 1–344.

51. Drake T A, Morrissey J H, Edgington T S: Selective cellular expression of tissue factor in human tissues. Implications for disorders of hemostasis and thrombosis. *Am J Path* 1989;1134: 1087.

52. Wilcox J N, Smith K M, Schwartz S M, Gordon D: Localization of tissue factor in the normal blood vessel wall and in the atherosclerotic plaque. *Proc Natl Acad Sci USA*. 1989;86:2839–2843.

53. Lin M -C, Almus-Jacobs F, Chen H -H, Parry G C N, Mackman N, Shyy J Y -J: Shear stress induction of the TF gene. *J Clin Invest* 1997;99:737–744.

54. Golino P, Ragni M, Cirillo P, Avvedimento V E, Feliciello A, Esposito N, Scognamiglio A, Trimarco B, Iaccarino G, Condorelli M, Chiariello M, Ambrosio G: Effects of tissue factor induced by oxygen free radicals on coronary flow during reperfusion. *Nature Medicine* 1996; 2(1):35–40.

55. Marmur J D, Rossikhina M, Guha A, Fyfe B, Friedrich, Mendiowitz M, Nernerson Y, Taubman M B: Tissue factor is rapidly induced in arterial smooth muscle after balloon injury. *J Clin Invest* 1993; 91;2253–2259.

56. Johnson K, Aarden L, Choi Y, Degroot F, Creasey A: The proinflammatory cytokine response to coagulation and endotoxin in whole blood. *Blood* 1996; 87(12):5051–5060.

57. Bloem U, Chen L, Konigsberg W H, Bach R: Serum stimulation of quiescent human fibroblasts induces the synthesis of tissue factor mRNA followed by the appearance of tissue factor antigen and procoagulant activity. *Journal of Cellular Physiology* 1989; 139:418–423.

58. Maynard J R, Dreyer B E, Stemerman M B, Pitlick F A: Tissue-factor coagulant activity of cultured human endothelial and smooth muscle cells and fibroblasts. *Blood* 1977; 50(5):387–395.

59. Moll T, Czyz M, Holzmoller H, Hofer-Warbinek R, Wagner F, Winkler H, Bach F H, Hofer E: Regulation of the tissue factor promoter in endothelial cells. *Journal of Biological Chemistry* 1995; 270(8):3849–3857.

60. Oeth P A, Parry G C N, Kunsch C, Nantermet P, Rosen C A, Mackman N: Lipopolysaccharide induction of tissue factor gene expression in monocytic cells is mediated by binding of c-Rel/p65 heterodimers to an NFKfl-like site. *Molecular and Cellular Biology* 1994; 14(6):3772–3781.

61. Taubman M B, J D, Rosenfield C -L, Guha A, Nichtberger S, Nemerson Y: Agonist-mediated tissue factor expression in cultured vascular smooth muscle cells. Role of Ca2+ mobilization and protein kinase C activation. *J Clin Invest* 1993; 91:547–552.

62. Carmeliet P, Mackman N, Moons L, Luther T, Gressens P, Vlaenderen I V, Demunck H, Kasper M, Breier G, Evrard P, Moller M, Risau W, Edgington T, Collen D: Role of tissue factor in embryonic blood vessel development. *Nature* 1996; 383; 73–75.

63. Feng N K, Yang Y C, Huang S C, Ou J T: Coagulation factor Xa stimulates platelet-derived growth factor release and mitogenesis in cultured vascular smooth muscle cells *J Clin Invest*. 1996; 98:1493–1501.

64. McNamara C A, Sarembock I J, Gimple L W, Fenton J W II, Coughlm S R, Owens G K: Thrombin stimulates proliferation of cultured rat aortic smooth muscle cells by a proteolytically activated receptor. *J Clin Invest* 1993; 91:94–98.

65. Molloy C J, Pawlowski J E, Taylor D S, Turner C E R, Weber H, Peluso M, Seiler S S: Thrombin receptor activation elicits rapid protein tyrosine phosphorylation and stimulation of the Raf-1/MAP kinase pathway preceding delayed mitogenesis in cultured rat aortic smooth muscle cells. *J Clin Invest* 1996; 97:1173–1183.

66. Sato Y, Asada Y, Maratsuka K, Hatekeyama K, Sumiyoshi A: Tissue factor induces migration of cultured aortic smooth muscle cells. *Thromb Hemost* 1996; 75:389–392.

67. Galis Z S, Kranzhofer R, Libby P: Thrombin promotes activation of matrix metalloproteinase-2 produced by cultured smooth muscle cells. *Faseb J.* 1995;9:A413 (Abstract).
68. Galis Z S, Sukhova G K, Lark M W, Libby P: Increased expression of matrix metalloproteinases and matrix degrading activity in vulnerable regions of human atherosclerotic plaques. *J Clin Invest* 1994;94:2493–2503.
69. Garabedian H D, Gold H K, Newell J B, Collen D: Accelerated thrombin generation during anticoagulation in patients with unstable angina pectoris (Letter). *Blood* 1994;83: 1155.
70. Lemarchand P, Jones M, Yamada I, Crystal R G: In vivo gene transfer and expression in normal uninjured blood vessels using replication-deficient recombinant adenovirus vectors. *Circ Res* 1993;72:1132–1138
71. Kass-Eisler A, Faick-Pedersen E, Elfenbein D H, Alvira M, Buttrick PM, Leinwand LA: The impact of developmental stage, route of administration and the immune system on adenovirus-mediated gene transfer. *Gene Ther* 1994; 1:395–395. Short duration
72. Gomez-Foix, A. M., Coats, W. S., Baque, S., Alam, T., Gerard, R. D., Newgard, C. B. Adenovirus-mediated transfer of the muscle glycogen phosphorylase gene into hepatocytes confers altered regulation of glycogen metabolism. *J Biol. Chem.* 1992; 267: 25129–12134.
73. Herz, J. & Gerard, R. D. Adenovirus-mediated transfer of low density lipoprotein receptor gene acutely accelerates cholesterol clearance in normal mice. *Proc. Natl. Acad. Sci. USA* 1993; 90: 2812–2816.
74. Gluzman Y, Reichi H, Solnick D: Helper-free adenovirus type 5 vectors. In Eukaryotic viral vectors (ed. Gluzman Y). Cold Spring Harbor Laboratory Press, Cold Spring Harbor, N.Y. 1982:187–192.
75. McGrory W J, Bautista D S, Graham F: A simple technique for the rescue of early region I mutations into human adenovirus type 5. *Virology* 1988;63:614–167.
76. Graham F L, van der Eb: A new technique for the assay of infectivity of human adenovirus DNA. *Virology* 1973;52:456–467.
77. Huyghe B G, Liu X, Sutjipto S, Sugarman B J, Horn M T, Shephard H M, Scandella C J, Shabram P: Purification of a type S recombinant adenovirus encoding human p53 by column chromatography. *Hum Gene Ther.* 1995; 6: 1403–1416

All patents and publications mentioned in this specification are indicative of the level of skill of those of knowledge in the art to which the invention pertains. All patents and publications referred to in this application are incorporated herein by reference to the same extent as if each was specifically indicated as being incorporated by reference, and to the extent that they provide materials and methods not specifically shown.

While the preferred embodiment of the invention has been shown and described, modifications thereof can be made by one skilled in the art without departing from the spirit and teachings of the invention. The embodiments described herein are exemplary only, and are not limiting. Many variations and modifications of the methods and compositions of the invention disclosed herein are possible and are within the scope of the invention. Accordingly, the scope of protection is not limited by the description set out above, but is only limited by the claims which follow, that scope including all equivalents of the subject matter of the claims.

What is claimed is:

1. A recombinant adenoviral vector comprising a human tissue factor pathway inhibitor (TFPI) cDNA operatively linked to a human cytomegalovirus immediate early promotor/enhancer and a simian leukemia virus (SV40) polyadenylation site.

2. A recombinant adenoviral vector comprising Ad.TFPI.

3. An anti-thrombotic agent comprising a recombinant adenoviral vector containing a human TFPI cDNA operatively linked to a human cytomegalovirus immediate early promotor/enhancer and a simian leukemia virus polyadenylation site.

4. Transduced vascular smooth muscle cells comprising a transgenic tissue factor pathway inhibitor cDNA.

5. An anti-thrombotic agent comprising a vascular smooth muscle cell, said cell producing transgenic human tissue factor pathway inhibitor.

6. The anti-thrombotic agent of claim 5 wherein said cell is administered to a human blood vessel.

7. A method of making a recombinant adenovirus vector comprising:
   ligating a cDNA encoding human full-length tissue factor pathway inhibitor into the BamHI site of the polylinker of the pACCMVpLpA plasmid to form the pLpA.TFPI shuttle plasmid;
   co-transfecting mammalian cells in tissue culture with said shuttle plasmid and plasmid pJM17;
   culturing the transfected cells until viral cytopathic effects appear;
   harvesting Ad.TFPI viral stock from said tissue culture;
   innoculating monolayers of mammalian cells in tissue culture with aliquots of high titer Ad.TFPI viral stock;
   harvesting culture medium and cells upon appearance of cytopathic effects;
   purifying recombinant virion particles containing Ad.TFPI.

8. A method of making an antithrombotic agent comprising:
   ligating a cDNA encoding human full-length tissue factor pathway inhibitor into the BamHI site of the polylinker of the pACCMVpLpA plasmid to form the pLpA.TFPI shuttle plasmid;
   co-transfecting mammalian cells in tissue culture with said shuttle plasmid and plasmid pJM17;
   culturing the transfected cells until viral cytopathic effects appear;
   harvesting Ad.TFPI viral stock from said tissue culture;
   innoculating monolayers of mammalian cells in tissue culture with aliquots of high titer Ad.TFPI viral stock;
   harvesting culture medium and cells after cytopathic effects appear;
   purifying recombinant virion particles containing Ad.TFPI;
   infecting vascular smooth muscle cells with purified Ad.TFPI virion particles, whereby said tissue factor pathway inhibitor cDNA is expressed by said cells.

9. A method of transducing a vascular smooth muscle cell comprising introducing into said cell a recombinant adenovirus vector containing a human tissue factor pathway inhibitor (TFPI) cDNA operatively linked to a human cytomegalovirus immediate early promotor/enhancer and a simian leukemia virus (SV40) polyadenylation site.

10. The method of claim 9 wherein said cell is a human vascular smooth muscle cell.

11. A method of producing hTFPI at a predetermined site in a blood vessel comprising exposing vascular smooth muscle cells at said site to a recombinant adenovirus vector containing a human tissue factor pathway inhibitor (TFPI) cDNA operatively linked to a human cytomegalovirus immediate early promoter/enhancer and a simian leukemia virus (SV40) polyadenylation site so that said TFPI cDNA is expressed and hTFPI is produced.

12. The method of claim 11 wherein at least $1 \times 10^6$ vascular smooth muscle cells are transduced.

13. A method of maintaining a therapeutic level of human TFPI at a predetermined blood vessel site comprising transfecting at least $1 \times 10^6$ vascular smooth muscle cells at said site with a recombinant adenovirus vector containing a human tissue factor pathway inhibitor (TFPI) cDNA operatively linked to a human cytomegalovirus immediate early promotor/enhancer and a simian leukemia virus (SV40) polyadenylation site such that said TFPI cDNA is expressed for at least 3 days.

14. A method of deterring thrombosis deposition at a predetermined blood vessel site comprising introducing a transgenic human tissue factor pathway inhibitor cDNA into vascular smooth muscle cells at said site so that the cDNA is expressed and deposition of thrombosis at said site is deterred.

15. The method of claim 14 wherein said introducing comprises exposing vascular smooth muscle cells at said site to a recombinant adenovirus vector containing a human tissue factor pathway inhibitor (TFPI) cDNA operatively linked to a human cytomegalovirus immediate early promotor/enhancer and a simian leukemia virus (SV40) polyadenylation site.

16. The method of claim 14 wherein said cells are human vascular smooth muscle cells.

17. A method of protecting a blood vessel site against thrombosis deposition comprising introducing a transgenic human tissue factor pathway inhibitor cDNA into vascular smooth muscle cells at said site so that the cDNA is expressed and the blood vessel site is protected against thrombosis deposition.

18. The method of claim 17 wherein said site comprises a balloon catheter injured artery site.

19. The method of claim 17 wherein said site comprises an atherosclerotic artery site.

20. The method of claim 17 wherein said site comprises a balloon catheter injured atherosclerotic site.

21. The method of claim 17 wherein said site comprises an angioplasty site.

22. The method of claim 17 wherein said site comprises an arteriovenous shunt.

23. The method of claim 17 wherein said site comprises an endovascular graft.

24. The method of claim 17 wherein said introducing comprises exposing said smooth muscle cells to a human tissue factor pathway inhibitor (TFPI) cDNA operatively linked to a human cytomegalovirus immediate early promotor/enhancer and a simian leukemia virus (SV40) polyadenylation site.

25. The method of claim 24 wherein said genetic alterating comprises exposing said smooth muscle cells to a human tissue factor pathway inhibitor (TFPI) cDNA operatively linked to a human cytomegalovirus immediate early promotor/enhancer and a simian leukemia virus (SV40) polyadenylation site.

26. A method of treating a site in a mammalian blood vessel that is at risk for thrombotic deposition and/or restenosis comprising genetically altering vascular smooth muscle cells at a site in said vessel such that said cells express a transgenic human tissue factor pathway inhibitor cDNA.

27. The method of claim 26 wherein said site comprises an atherosclerotic artery site, a balloon catheter injured artery site, an angioplasty site, arteriovenous shunt or an endovascular graft.

28. The method of claim 26 wherein said genetic altering comprises:
   ligating a cDNA encoding human full-length tissue factor pathway inhibitor into the BamHI site of the polylinker of the pACCMVpLpA plasmid to form the pLpA.TFPI shuttle plasmid;

co-transfecting mammalian cells in tissue culture with said shuttle plasmid and plasmid pJM17;

culturing the transfected cells until viral cytopathic effects appear;

harvesting Ad.TFPI viral stock from said tissue culture;

innoculating monolayers of mammalian cells in tissue culture with aliquots of high titer Ad.TFPI viral stock;

harvesting culture medium and cells after cytopathic effects appear;

purifying recombinant virion particles containing Ad.TFPI; and infecting at least $1 \times 10^6$ vascular smooth muscle cells situated at a predetermined site in said vessel with said purified Ad.TFPI virion particles, whereby a therapeutic level of hTFPI is produced by said cells.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:Forward Primer

<400> SEQUENCE: 1
aatcttgccc ctgcccctct ta        22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:Reverse Primer

<400> SEQUENCE: 2
aaaccattcg gaccatcttc acaa        24